United States Patent
Beaupre

(10) Patent No.: US 11,045,223 B2
(45) Date of Patent: Jun. 29, 2021

(54) MODULAR SIGNAL INTERFACE SYSTEM AND POWERED TROCAR

(71) Applicant: REACH SURGICAL, INC., Tianjin (CN)

(72) Inventor: Jean Beaupre, Alexandria, KY (US)

(73) Assignee: REACH SURGICAL, INC., Tianjin (CN)

( * ) Notice: Subject to any disclaimer, the term of this patent is extended or adjusted under 35 U.S.C. 154(b) by 70 days.

(21) Appl. No.: 15/576,347

(22) PCT Filed: Dec. 11, 2016

(86) PCT No.: PCT/US2016/066044
§ 371 (c)(1),
(2) Date: Nov. 22, 2017

(87) PCT Pub. No.: WO2017/100728
PCT Pub. Date: Jun. 15, 2017

(65) Prior Publication Data
US 2018/0206884 A1    Jul. 26, 2018

Related U.S. Application Data

(60) Provisional application No. 62/266,149, filed on Dec. 11, 2015.

(51) Int. Cl.
*A61B 17/34* (2006.01)
*A61B 18/00* (2006.01)
(Continued)

(52) U.S. Cl.
CPC .......... *A61B 17/3476* (2013.01); *A61B 18/00* (2013.01); *A61B 18/14* (2013.01);
(Continued)

(58) Field of Classification Search
CPC ..... A61B 17/3476; A61B 18/00; A61B 18/14; A61B 2017/00482; A61B 17/320068;
(Continued)

(56) References Cited

U.S. PATENT DOCUMENTS 2,170,287 A    8/1939   Kinnebrew
3,363,214 A    1/1968   Wright
(Continued)

FOREIGN PATENT DOCUMENTS

EP    0888747 A1    1/1999
WO    2015025547 A1   2/2015
(Continued)

OTHER PUBLICATIONS

International Search Report and Written Opinion for PCT/US2016/066044, dated Apr. 28, 2017.
(Continued)

*Primary Examiner* — Elizabeth Houston
*Assistant Examiner* — Michael G Mendoza
(74) *Attorney, Agent, or Firm* — Porter Wright Morris & Arthur LLP

(57) ABSTRACT

A modular signal interface system for providing electrical communication with a surgical instrument when the surgical instrument is inserted into a cannula of a trocar. The system includes a signal interface adapter and an instrument connector. The signal interface adapter is provided on, or adapted to be mounted on a trocar, and includes central aperture extending therethrough and a proximal face having a plurality of conductive contacts. The instrument connector is provided on or adapted to be mounted on a shaft of a surgical instrument, and includes a central aperture extending therethrough and a distal face having a plurality of conductive contacts. The signal interface adapter and the instrument connector are adapted for mating engagement
(Continued)

such that, when matingly engaged, their central apertures are axially aligned and predetermined ones of the plurality of contacts of the signal interface adapter are in conductive contact with predetermined ones of the plurality of contacts of the instrument connector.

21 Claims, 20 Drawing Sheets

(51) Int. Cl.
   *A61B 17/00* (2006.01)
   *A61B 17/32* (2006.01)
   *A61N 7/00* (2006.01)
   *A61B 18/14* (2006.01)

(52) U.S. Cl.
   CPC ........ *A61N 7/00* (2013.01); *A61B 17/320068* (2013.01); *A61B 2017/00477* (2013.01); *A61B 2017/00482* (2013.01); *A61B 2017/347* (2013.01); *A61B 2018/00178* (2013.01)

(58) Field of Classification Search
   CPC ........... A61B 2018/00178; A61B 2017/00477; A61B 2017/347; A61N 7/00; H01R 2201/12
   See application file for complete search history.

(56) References Cited

U.S. PATENT DOCUMENTS

| | | |
|---|---|---|
| 3,808,577 A | 4/1974 | Mathauser |
| 3,810,258 A | 5/1974 | Mathauser |
| 4,317,969 A | 3/1982 | Riegler et al. |
| 4,669,791 A | 6/1987 | Savill |
| 5,829,987 A | 11/1998 | Fritsch et al. |
| 5,916,215 A | 6/1999 | Long et al. |
| 5,921,783 A | 7/1999 | Fritsch et al. |
| 5,925,041 A | 7/1999 | Long et al. |
| 5,954,520 A | 9/1999 | Schmidt |
| 5,961,514 A | 10/1999 | Long et al. |
| 6,106,519 A | 8/2000 | Long et al. |
| 6,117,132 A | 9/2000 | Long et al. |
| 6,187,002 B1 | 2/2001 | Long et al. |
| 6,206,875 B1 | 3/2001 | Long et al. |
| 7,311,526 B2 | 12/2007 | Rohrbach et al. |
| 7,351,066 B2 | 4/2008 | DiFonzo et al. |
| 8,449,460 B2 | 5/2013 | Duke et al. |
| 9,112,304 B2 | 8/2015 | Rohrbach et al. |
| 2005/0070947 A1 | 3/2005 | Franer et al. |
| 2013/0324991 A1* | 12/2013 | Clem ............. A61B 17/320068 606/33 |
| 2015/0057653 A1 | 2/2015 | Sugiyama |
| 2015/0359565 A1 | 12/2015 | Matsui |

FOREIGN PATENT DOCUMENTS

| | | |
|---|---|---|
| WO | 2016135945 A1 | 9/2016 |
| WO | 2016157504 A1 | 10/2016 |

OTHER PUBLICATIONS

European Search Report and Opinion for EP16874015.6, dated Oct. 17, 2018.
European Search Report and Opinion for EP19172952.4 (div. of 16874015.6), dated Jul. 7, 2019.

* cited by examiner

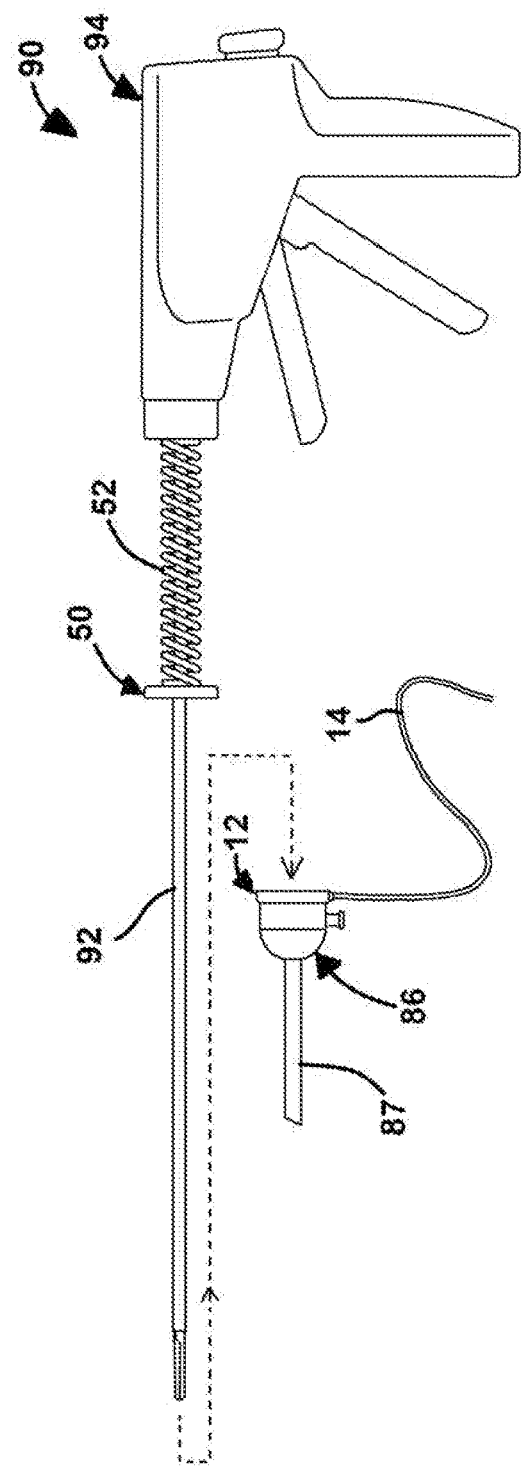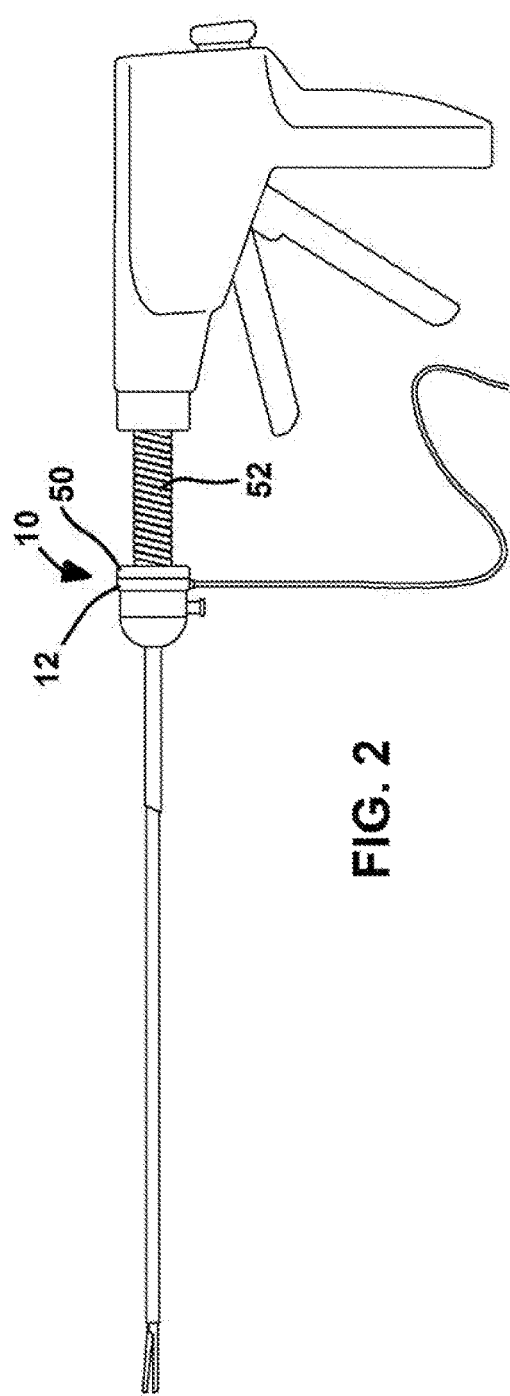

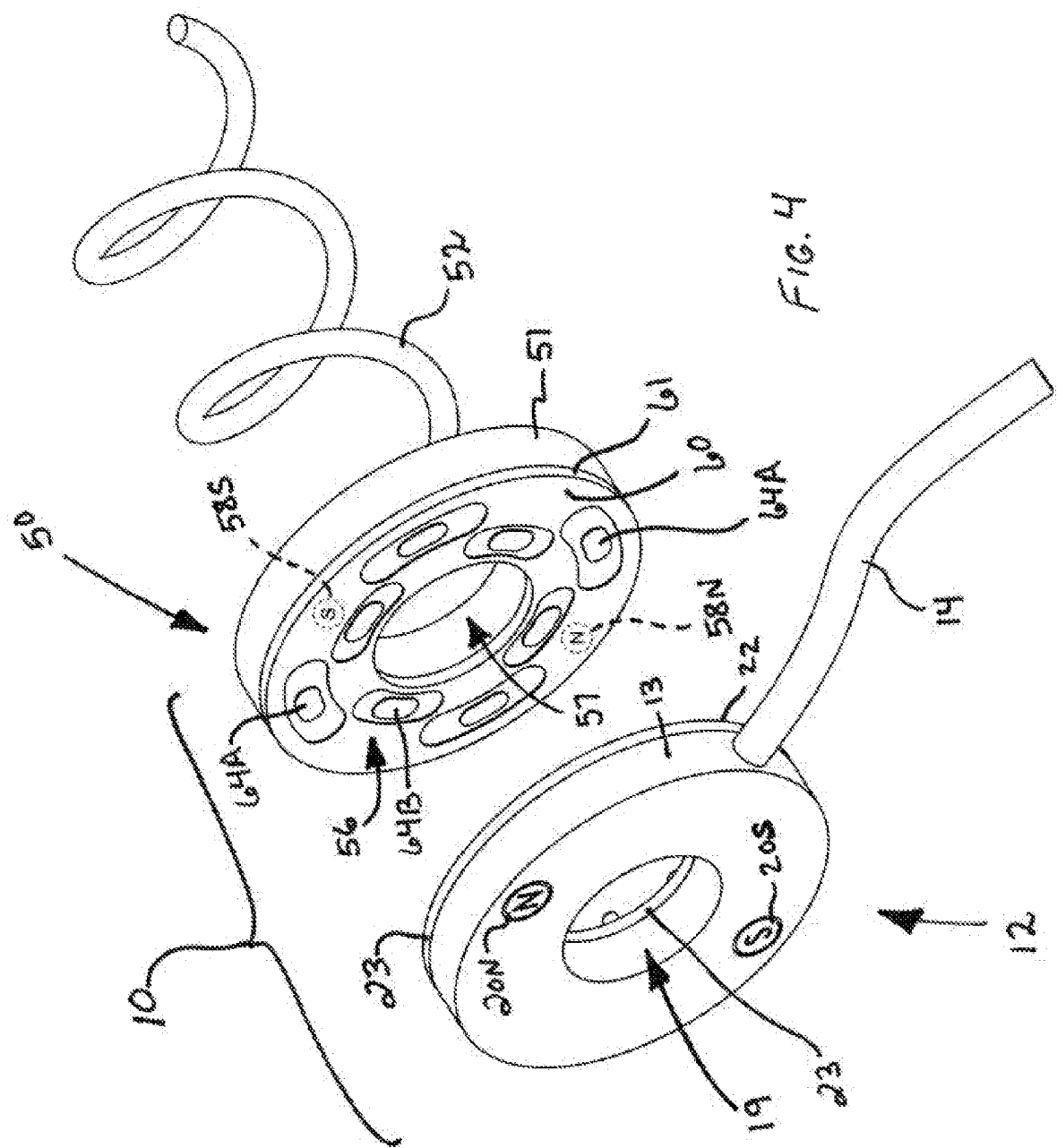

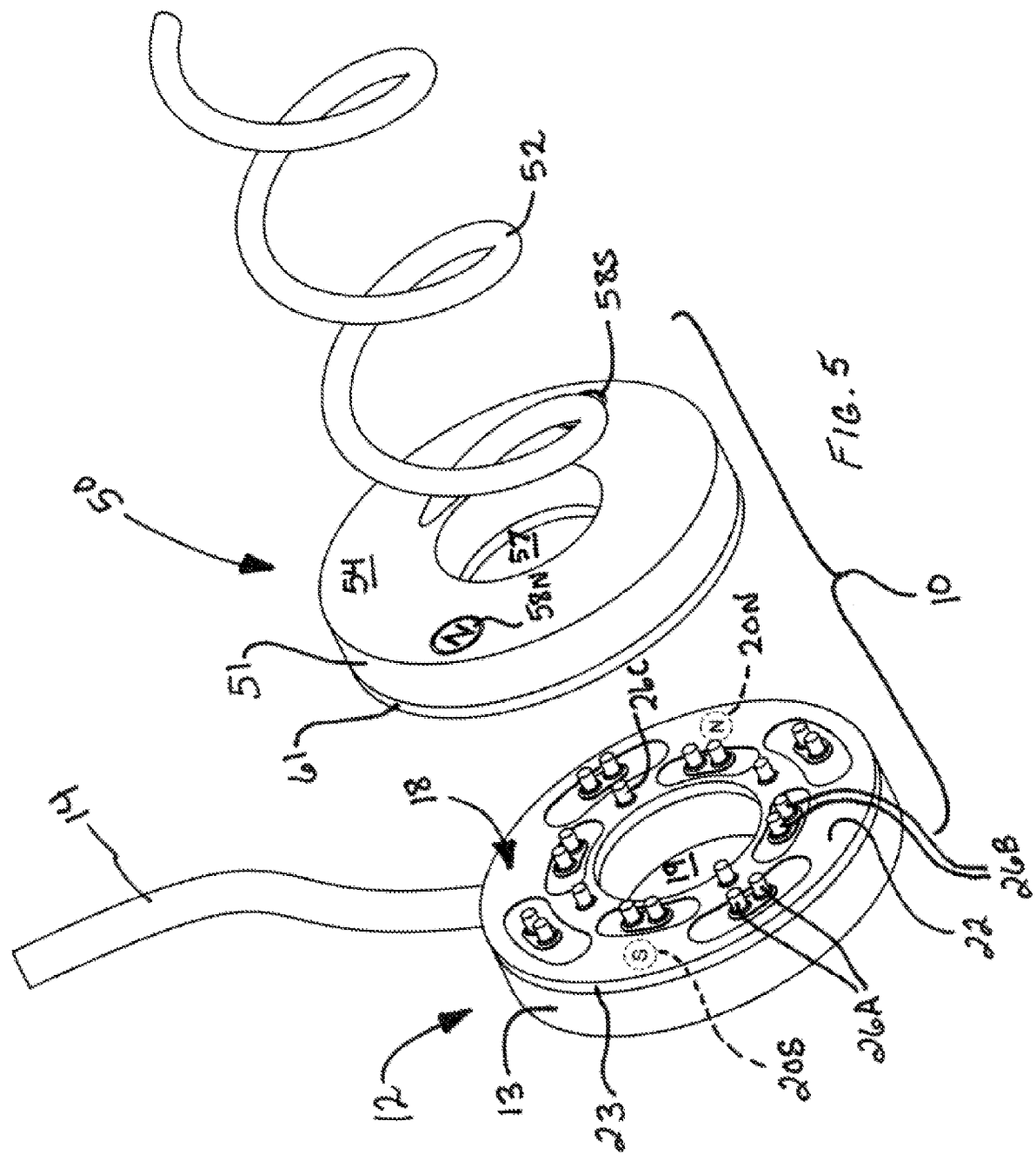

MODULAR SIGNAL INTERFACE SYSTEM AND POWERED TROCAR

CROSS REFERENCE TO RELATED APPLICATIONS

This application claims priority to U.S. Provisional Patent Application No. 62/266,149, filed on Dec. 11, 2015, entitled "MODULAR SIGNAL INTERFACE SYSTEM AND POWERED TROCAR." The entire disclosure of the foregoing provisional patent application is incorporated by reference herein.

BACKGROUND

Endoscopic medical procedures, particularly endoscopic surgery, continue to become more and more prevalent. In these procedures, one or more openings in tissue are created in order to provide access to anatomical cavities and other internal structures within a patient. As used herein, "endoscopic" refers to procedures which are performed through one or more openings (e.g., incisions) in a patient's tissue, such as one or more openings made in the abdominal wall. Various instruments, including, for example, tubular optical instruments (e.g., endoscopes) are inserted into the patient though these openings to manipulate internal structures, perform various procedures, and/or, in the case of an endoscope, to provide vision within the patient. The term "endoscopic" is generic to, and therefore includes, for example, terms such as "laparoscopic" and "arthroscopic," which refer to the use of an endoscope in a particular region of the body.

Whether the instrument to be inserted into the patient is an endoscope (through which other instruments may thereafter be inserted) or a simple surgical instrument such as a grasper, a cannula is first passed through an opening in the tissue wall into an anatomical cavity (or other internal region in the patient). Thereafter, the endoscope or other surgical instrument is inserted through the cannula into the anatomical cavity. The cannula provides a passageway which remains available for use during the surgical procedure, providing access to the anatomical cavity and the ability to insert and remove various instruments throughout the procedure.

One commonly-employed instrument for penetrating tissue and positioning a cannula therein is referred to as a "trocar." Trocars generally comprise an obturator for creating an opening in tissue, and an outer cannula (also referred to as the trocar tube or sleeve). The distal end of the cannula is positioned against the patient's skin, and the obturator is positioned within the interior of the cannula. With the sharp distal end of the obturator protruding beyond the distal end of the cannula, the distal end of the obturator is urged through the tissue (e.g., skin, underlying fascia, and fat) until it enters the targeted anatomical cavity. The cannula is urged through the tissue opening created by the obturator, typically following closely behind the sharp distal tip of the obturator. Once the distal end of the cannula is in the desired location in the anatomical cavity, the obturator is withdrawn from the cannula. The cannula remains in place, and provides a passageway through which access to the anatomical cavity is provided.

In many instances, various type of powered or otherwise wired surgical instruments are used in endoscopic procedures, including, for example, endoscopes, electrosurgical instruments (bipolar and monopolar, e.g., bipolar forceps), ultrasonic instruments (e.g., ultrasonic blades), DC-powered devices, etc. However, each of these instruments typically requires one or more cables for transmitting power and/or data between the instrument and other equipment (e.g., a power supply, an RF or ultrasonic generator, a signal processing device, a display device, etc.) in the surgical environment. Electrical cables and the like can be cumbersome during surgery or other endoscopic medical procedures, often interfering with the procedure itself. This problem (and others) are exacerbated by the need to use multiple powered or otherwise wired instruments during a procedure. Furthermore, although a variety of cordless surgical instruments such as ultrasonic cutting/cautery and radio frequency cutting/cautery instruments have been developed, such instruments rely upon a power supply (e.g., a battery) located within the instrument itself. This adds additional weight as well as manufacturing costs.

While a variety of devices and techniques may exist for providing electrical communication with an instrument used through a trocar cannula, it is believed that no one prior to the inventor(s) has made or used an invention as described herein.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

FIG. 1 depicts a schematic view of one embodiment of a modular signal interface system, comprising a signal interface adapter mounted on a trocar cannula housing and an instrument connector mounted on the shaft of a surgical instrument.

FIG. 2 depicts a schematic view of the embodiment of FIG. 1, wherein the signal interface adapter and instrument connector are in mating engagement, with the shaft of the surgical instrument fully extended into the trocar cannula.

FIG. 4 is a perspective view of the modular signal interface system of FIG. 1, wherein the signal interface adapter has been removed from the trocar cannula housing and the instrument connector has been removed from the surgical instrument.

FIG. 5 is a perspective view of the modular signal interface system of FIG. 4, wherein the viewing angle is rotated from that of FIG. 4 such that the proximal face of the signal interface adapter is visible (rather than the distal face, as in FIG. 4).

FIGS. 9 and 10 are perspective views of an alternative embodiment of a modular signal interface system, wherein FIG. 9 depicts the proximal side of the signal interface adapter and FIG. 10 depicts the distal side of the instrument connector.

FIGS. 13 and 14 are perspective views of yet another alternative embodiment of a modular signal interface system, wherein FIG. 13 is a view similar to that of FIG. 4 and of FIG. 14 is a view similar to that of FIG. 5.

Figure 3:
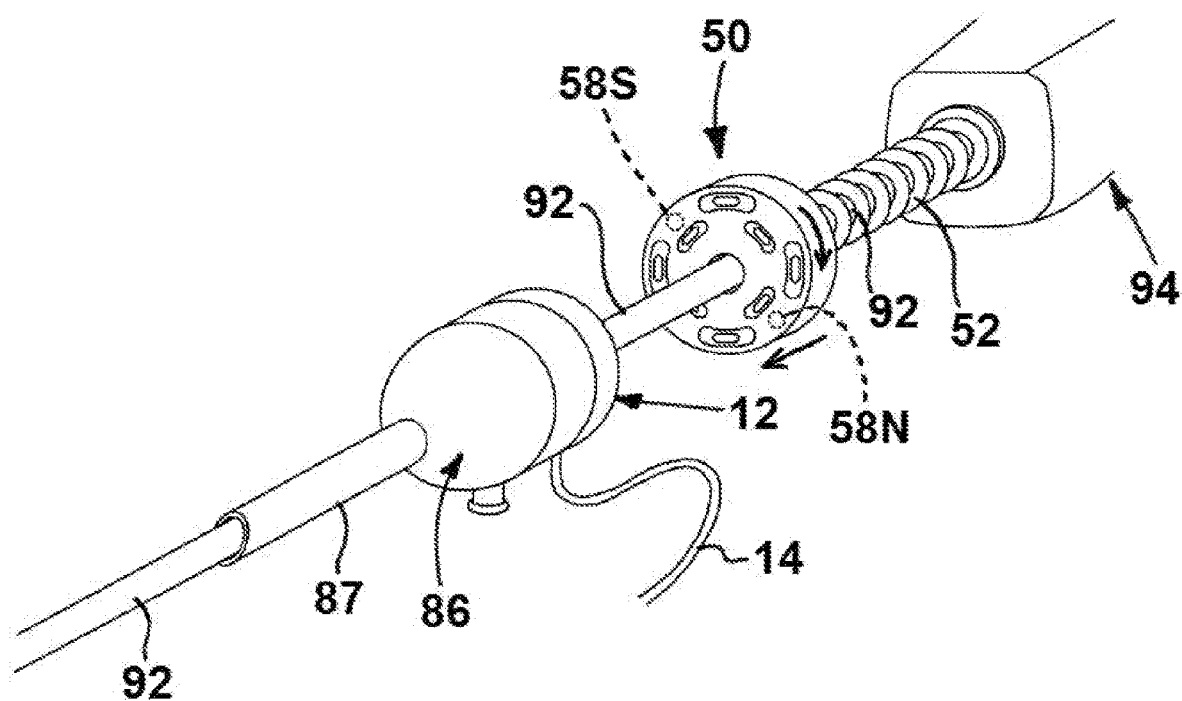
FIG. 3 depicts a schematic view of the embodiment of FIG. 1, wherein the instrument connector is being advanced towards the signal interface adapter under the influence of magnetic force.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

As used herein, unless the context indicates otherwise, the term "cable" is intended to encompass signal-conducting devices comprising an assembly of two or more conductors such as wires (single or multiple strand), and other types of physical conduits, traces or lines that conduct electrical signals, whether power signals (e.g., DC or AC power) or communication signals (e.g., a voltage or current indicative of a sensed condition, a video, image or audio signal, etc.). As also used herein, the phrase "in electrical communication" means that the electrical signals can be transmitted between the two components, such as via one or more wires, conduits, traces, lines, terminal blocks, posts, solder joints, integrated circuit traces, and the like, or through direct contact of the two components.

Embodiments of the present disclosure provide a modular signal interface system for communicating one or more electrical signals between, for example, a surgical cannula and an instrument inserted into the cannula. The modular signal interface system generally includes a signal interface adapter provided on, or configured to be mounted on, a cannula, and an instrument connector configured to matingly engage the cannula-mounted signal interface adapter so as to provide electrical communication between the signal interface adapter and the instrument connector over one or more communication channels. In this manner, one or more electrical signals can be communicated between the signal interface adapter and the instrument connector. The mating engagement of the signal interface adapter and the instrument connector allows one or more electrical signals to pass between the signal interface adapter and the instrument connector. The electrical signals can comprise power signals (e.g., current or voltage) and/or communication signals (e.g., a sensor signal).

In one specific embodiment, the signal interface adapter is configured to be affixed to a cannula (permanently or removably), particularly at the proximal end of the cannula (i.e., the end which remains outside of the patient during use). A cable, operatively attached to the signal interface adapter, communicates one or more electrical signals between the signal interface adapter and another device (e.g., a power supply, an RF or ultrasonic generator, a signal processing device, a display device, etc.). The signal interface adapter provides an interface for electrical communications between the instrument connector and the other device connected to the interface adapter, without the need for a wired connection between the surgical instrument itself and the other device.

By way of example, in some embodiments the mating engagement between the interface adapter and the instrument connector allows power for operating a surgical instrument to be delivered to the instrument via the signal interface adapter rather than a cable attached to, and extending away from the surgical instrument itself. In this embodiment, there is no need for a cord or other electrical conduit to be attached to the instrument that could interfere with medical procedures or a medical practitioner performing medical procedures. Instead, external electrical connectivity (e.g., to a power supply or other device) is provided by the cannula-mounted signal interface adapter and a cable or other conduit(s) attached thereto.

In some embodiments, the modular signal interface system allows a variety of cordless, signal-associated instruments such as various powered surgical instruments to be used with a cannula, such that electrical signals necessary for operation of the instrument (e.g., power, sensor signals, etc.) are communicated via the signal interface adapter on the cannula rather than by a cord attached to the surgical instrument itself. This can obviate the need, for example, to physically connect each instrument to an external power supply (e.g., via a cable) prior to use. Instead, the interface adapter on the cannula is connected to an external power supply, and the mating engagement of the interface adapter and the instrument connector allows power to be supplied to the instrument via the interface adapter on the cannula. Multiple surgical instruments can be used in this way during a surgical procedure, with only a single cable supplying power to each instrument via the signal interface adapter. In addition, in some embodiments the signal interface adapter is configured such that it will not interfere with the use of conventional surgical instruments (i.e., instruments used without the instrument connector of the signal interface system) through the cannula.

Mating engagement of the interface adapter and the instrument connector is accomplished in a variety of ways. In some embodiments, mating engagement is accomplished magnetically. Complementary magnetic regions on both the interface adapter and the instrument connector provide not only the necessary force for magnetically engaging the interface adapter and instrument connector, but also are arranged so as to ensure or facilitate proper alignment of that engagement. When the interface adapter and the instrument connector are alignably engaged with one another, conductive contacts on the interface adapter will be in contacting relationship with corresponding conductive contacts on the instrument connector such that electrical continuity is established between the contacts on the interface adapter and the corresponding contacts on the instrument connector. This electrical continuity allows electrical signals to pass between predetermined pairs of contacts that are in contacting relationship with one another. Aligned engagement of the interface adapter and the instrument connector ensures that electrical signals pass through the appropriate pairs of contacts.

The conductive contacts can have any of a variety of forms, including planar contacts as well as elongated contacts (e.g., conductive pins such as pogo pins). The conductive contacts can be have the same configuration on both components (e.g., both components having planar contacts), or they can be different (planar contacts on one component and elongated contacts on the other). Similarly, more than one type of contact (planar and elongated) cane be provided on one or both components. In some embodiments, one or more of the conductive contacts are resiliently biased away from the component on which they are provided. By way of example, spring-biased pin contacts (e.g., pogo pins can be employed). In the case of planar contacts, a resilient member such as biasing members formed of a resilient polymer or springs can be located beneath planar contacts for biasing purposes.

In some embodiments, the contacts on one or both of the components comprise a first plurality of planar conductive contacts (e.g., conductive islands in various shapes such as curved ovals). Alternatively, one of the components (e.g., the signal interface adapter) includes a plurality of conductive pin contacts configured to conductively contact predetermined planar contacts on the other component (e.g., the instrument connector). In addition, in some embodiments the contacts on one or both of the signal interface adapter and the instrument connector further include at least one apertured planar conductive contact having a plurality of apertures therein, with each of the first plurality of planar or pin contacts located within the boundary of one of said plurality of apertures and spaced. In one specific embodiment, the apertured planar conductive contact is in the form of a conductive annular ring having a central aperture as well as a plurality of peripheral apertures, with each of the planar or pin contacts located within one of the peripheral apertures. By locating the planar/pin contacts within the peripheral apertures, the planar/pin contacts are electrically isolated from (i.e., not in conductive contact with) one another as well isolated from the conductive ring itself. In some embodiments a conductive annular ring is provided on both components, while in other embodiments the conductive annular ring is provided on only one of the components. In some embodiments one or both components includes one or more additional conductive contacts arranged to conductively contact the conductive annular ring (or other apertured planar contact) on the other component.

In some embodiments, the signal interface adapter is configured for removable attachment to a trocar cannula. For example, in some embodiments the interface adapter is adapted for removable attachment to the proximal end of a cannula housing after the obturator assembly has been removed from the cannula. In other embodiments, the signal interface adapter is integrated into the cannula assembly, particularly at the proximal end thereof, and therefore is not intended to be remove from the cannula.

In general, the surgical instruments with which the modular signal interface system described herein can be used have an elongate shaft that is adapted to be received within the interior passageway of a surgical cannula. Embodiments of the instrument connector component of the interface system include a central aperture through which the instrument shaft is received. In particular embodiments, the instrument shaft is slidingly received through the central aperture of the instrument connector such that the connector can slide axially and rotatingly along at least a portion of the instrument shaft. As further described herein, the instrument connector will not interfere with the use of the instrument within the trocar cannula, while facilitating the mating engagement between the instrument connector and the interface adapter since the connector is able to slide along and rotate about the instrument shaft so as to matingly engage the interface adapter by magnetic attraction.

In some embodiments, the instrument connector is electrically connected to the instrument (e.g., to the instrument body) by a cable, which, in some instances, can be coiled around the exterior of the instrument shaft between the instrument connector and the instrument body (as seen in FIGS. 1-3). In some of these arrangements the length of the cable is such that the instrument connector cannot slide off of the instrument shaft without first disconnecting the cable from the instrument and/or from the instrument connector.

In addition, in certain embodiments, particularly for instruments having an instrument shaft that is rotatable with respect to the instrument body (i.e., the instrument handle), the cable is rotatably connected to the instrument such that the cable rotates along with the instrument shaft while still maintaining electrical connectivity with the instrument. In this manner, the cable between the instrument connector and the surgical instrument will not limit rotation of the instrument shaft with respect to the instrument handle. In alternative embodiments, the instrument connector is electrically connected to the instrument body (or other portion of the instrument) by an internally routed cable.

The modular signal interface system described herein can be used with a wide variety of signal-associated surgical instruments. As used herein, a "signal-associated surgical instrument" is a surgical instrument that receives and/or supplies one or more electrical signals to an external device, wherein those electrical signals can comprise power signals (e.g., current or voltage) and/or communication signals (e.g., a sensor signal). Signal-associated surgical instruments include powered surgical instruments (particularly those configured for use though a cannula), as well as, for example, instruments used for: ultrasonic cutting/cautery, ultrasonic imaging, focused ultrasound, radio frequency cautery, radio frequency cutting, radio frequency ablation, stapling, sensing, imaging, measuring, robotic, haptic, cutting, grinding, clamping, thermal, radio-isotopic, drug delivery, biopsy, hyperspectral imaging, insufflation, and/or suturing.

FIGS. 1-8 depict schematic illustrations of one embodiment of a modular signal interface system (10) comprising a signal interface adapter (12) and an instrument connector (50). In the embodiment shown in these figures, signal interface adapter (12) is mounted on the proximal end of a trocar cannula housing (86) having a cannula (87) extending distally therefrom. The instrument connector (50) is slidingly mounted on the elongate shaft (92) of a powered surgical instrument (90) that extends distally away from the instrument body (94) (also commonly referred to as the instrument handle). In this particular example, the instrument (90) is an electrosurgical cutter/stapler device of known construction.

As best seen in FIGS. 4 and 5, the signal interface adapter (12) generally comprises a housing (13) and a cover plate (23) mounted thereto. A main cable (14) is operatively connected to the signal interface adapter (12) at one end, and the other end of the main cable (14) (not shown) is adapted for operative connection to an external electrical device (e.g., a power supply or an RF or ultrasonic generator) for supplying electrical signals to, and in some instances receiving electrical signals from, the interface adapter (12). Main cable (14) can include any number of electrical conduits, in some instances corresponding to the number of distinct communication channels established when the contacts on the interface adapter (12) conductively contact the corresponding contacts on the instrument connector (50).

In the embodiment shown in FIGS. 1-8, and as further explained below, the mating faces of each of the interface adapter and the instrument connector components have nine conductive contacts arranged about a central aperture provided in each component, with each contact on a component oriented for conductively contacting a corresponding contact on the other component. Thus, in this particular embodiment, nine distinct communication channels between the signal interface adapter (12) and instrument connector (50) are established when these two components are in proper mating engagement. Similarly, main cable (14) has, for example, nine independent electrical conduits (e.g., wires) inside an outer sheath—one conduit for each communication channel provided by the modular signal interface system (10). While the use of these nine channels will vary, in the embodiment shown, four of the channels are used for transmitting power signals, and five are used for transmitting communication signals (including one that is used as a "sense line," as further described herein). It will be understood, of course, that any number of mating contacts, and hence communication channels, can be provided. Similarly, the number of mating contacts and communication channels need not correspond to the number of conductors in cable (14). In some instances, the number of mating contacts and communication channels is greater than the number of electrical conduits of cable (14) (e.g., when electronic circuitry within interface adapter (12) and/or instrument connector (50)/instrument (90) require one or more communication channels in addition to those having a corresponding conductor in cable (14)). In other instances, the number of mating contacts and communication channels is less than the number of electrical conductors in main cable (14) (e.g., when there are one or more redundant conductors in cable (14), such as for safety reasons).

As best seen in FIGS. 4 and 5, the instrument connector (50) generally comprises a housing (51) and a cover plate (61) mounted thereto. An instrument cable (52) is operatively connected between the instrument connector (50) and the instrument body (94) for transmitting electrical signals between the connector (50) and the instrument body (94). Once again cable (52) can include any number of electrical conductors (e.g., wires) therein, in some instances corresponding to the number of communication channels established when the contacts on the interface adapter (12) conductively contact the corresponding conductive contacts on the instrument connector (50). For example, in the embodiment shown, cable (52) has nine independent conductors (wires) inside an outer sheath—one conductor for each communication channel provided by the modular signal interface system (10). In other instances, the number of mating contacts on a component (12 or 50) and/or the number of communication channels between the two components (12, 50) is greater than the number of electrical conductors of the cable (52) (e.g., when a particular instrument does not require use of the full complement of communication channels).

In the embodiment depicted in FIGS. 1-8, the cables (14, 52) are non-detachably coupled to their respective component (i.e., interface adapter (12) and instrument connector (50)), as shown. In addition, cable (52) is non-detachably coupled to the instrument body (94)—in this case, internally within the instrument body (94). For instruments wherein the instrument shaft is rotatable with respect to the instrument body, the proximal end of the cable (52) can be mounted so as to rotate with the instrument shaft while still maintaining electrical connectivity. As best seen in FIG. 5, the distal end of cable (52) is coupled to the instrument connector (50) through the proximal face (54) of housing (51). As best seen in FIG. 4, cable (14) is coupled to the interface adapter (12) through the sidewall of housing (13).

As an alternative to non-detachably coupling the cables, one or both of the cables (14, 52) can be detachably connected to their respective interface adapter (12) and instrument connector (50)/instrument body (94), such as by using suitable male and female electrical couplings (e.g., RJ-type connectors, D-sub connectors, Amphenol® brand connectors, Molex® brand connectors, and other electrical coupling systems known to those skilled in the art or hereafter developed). The use of such couplings allow one or both of the cables (14, 52) to be detached from their respective interface adapter (12) and instrument connector (50)/instrument body (94). In some instances this is desirable, for example, to allow cable (14) to be detached from the interface adapter (12) when it is not needed for providing electrical communication to a surgical instrument. This can be particularly useful when the interface adapter (12) is not removably affixed to the trocar cannula housing (86), or when it is not desirable or convenient to remove the interface adapter (12) from the trocar cannula housing (86).

Similarly, a detachable coupling of cable (52) to instrument body (94) can be advantageous, for example, in that it allows instrument connector (50) to be employed with multiple instruments and/or removed from the instrument when it is not needed. Detachable coupling of the cables (14, 52) is also useful for cleaning and sterilization purposes, as well as to allow for the replacement of a cable (particularly when the cables (14, 52) are off-the-shelf components).

Turning to FIGS. 4 and 5, each of interface adapter (12) and instrument connector (50) are annular in shape, having central apertures (19, 57) extending therethrough. These apertures (19, 57) are sized and configured to slidably and rotatably receive instrument shaft (92) therethrough. Upon mating engagement of interface adapter (12) and instrument connector (50) their respective central apertures (19, 57) are axially aligned with each other and with the cannula of the trocar on which the interface adapter (12) is mounted or provided. For example, the central apertures (19, 57) can be sized to have a diameter equal to or slightly greater than the inner diameter of the cannula (87) of the trocar with which the system is to be used. In some embodiments, the diameter of the central aperture (19) of the signal interface adapter (12) is slightly larger than the diameter of the central aperture (57) of the instrument connector (50) as well as the internal diameter of the trocar cannula. By way of example only, the central apertures (19, 57) can have a diameter of about 3 to about 100 mm. In one particular embodiment, the central apertures (19, 57) can have a diameter of about 13 mm (e.g., 12.7 mm), approximately the same as the inner diameter of a "10 mm" trocar (wherein the "10 mm" refers to the size of the instrument received within the trocar cannula). Such sizing allows the modular signal interface system to be used with both "5 mm" and "10 mm" trocars—the most commonly used sizes of trocars. In some instances the central aperture (19) of the signal interface adapter (12) is about 1 to 5 mm larger than the diameter of the central aperture (57) of the instrument connector (50) and the internal diameter of the trocar cannula.

In the embodiment shown in FIGS. 1-8, interface adapter (12) is non-removably affixed to the proximal end of the trocar cannula housing (86) (i.e., it is an integral part of the trocar cannula housing). In the alternative embodiment shown in FIGS. 13-31 and described further herein, the signal interface adapter is removably attachable to the trocar, such as by a spring clip arrangement configured to matingly engage with features on the trocar cannula housing. It will also be understood that the shape of signal interface adapter (12) and instrument connector (50) shown in FIGS. 1-8 is merely exemplary. It will also be understood that the term "annular," as used herein, includes not only structures having a circular central aperture and corresponding circular outer perimeter concentric with the central aperture, but also various other outer perimeter shapes such as oval, square, rectangular, polygonal, etc. In some embodiments, the outer perimeter shapes of signal interface adapter (12) and instrument connector (50) can be similar to that of the trocar cannula housing, particularly the shape of the proximal end of the trocar cannula housing.

As also seen in FIGS. 4 and 5, a pair of opposite polarity magnetic regions, e.g., from magnets (20N, 20S), are provided on signal interface adapter (12) adjacent the proximal face (18) thereof. Similarly, a pair of opposite polarity magnetic regions, e.g., from magnets (58N, 58S), are provided on instrument connector (50) adjacent the distal face (56) thereof. Although the opposite polarity magnetic regions can be arranged at any of a variety of circumferentially spaced-apart locations on the interface adapter (12) and instrument connector (50), in the embodiment shown the magnets of each component (12, 50) of the interface system are located 180 degrees apart (i.e., on opposite sides of the central aperture), with the orientation of their polarities reversed. Such an arrangement maximizes magnetically induced rotational torque on the instrument connector (50) during mating engagement of the two components (12, 50). Although a single magnet can be used on each component (12, 50), with the magnets arranged to provide magnetic fields of opposite polarity adjacent the mating faces of the components, the use of two magnets arranged to provide magnetic fields of opposite polarity adjacent the mating face of each component not only increases the magnetic forces that pull the components into alignment, but also helps to ensure that the instrument connector (50) cannot be advanced towards the interface adapter (12) in such a way that the magnetic forces are unable to pull the components (12, 50) into proper, mating engagement. In addition, although more than two magnetic regions can be used on each of the components (12, 50), at least one magnetic region on each component should have a polarity opposite to other magnetic regions on that component. Also, when the signal interface system (10) is designed such that there is but one proper rotational alignment of the interface adapter (12) and the instrument connector (50), and more than two magnetic regions are provided on each component (12, 50), the magnetic regions are arranged so as to allow only one rotational orientation of magnetically coupled mating engagement of the components.

As best seen in FIGS. 4 and 5, and the isolated views of FIGS. 6A-B and 7A-B, the proximal face (18) of the signal interface adapter (12) and the distal face (56) of the instrument connector (50) each include a plurality of conductive contacts arranged such that, when the components (12, 50) are in mating engagement (FIG. 2), a predetermined one or more of the contacts on one component (12, 50) will be in contacting relationship with a predetermined one or more of the contacts on the other component (12, 50). Any of a variety of types of conductive contacts can be used, in any of a variety of arrangements, and those shown and described herein are merely exemplary ones of many possible types and arrangements of conductive contacts.

In the embodiment shown in FIGS. 1-8, each contacting face (18, 56) of the two components (12, 50) includes an annular conductive ring (22, 60) having an outer perimeter generally corresponding to that of its respective component (12, 50) and a central aperture (25, 63) corresponding to the central aperture (19, 57) of its respective component (12, 50). In the example shown, conductive rings (22, 60) generally have the same configuration except that the conductive ring (22) of the signal interface adapter (12) includes an additional set of apertures through which contacts (e.g., in the form of pogo pins (26C)) extend, as more fully described below (and shown, for example, in FIGS. 6A and 6B). It will be understood that the conductive rings (22, 60) can have a variety of other configurations, such as conductive rings that have an outer perimeter that is smaller than the outer perimeter of the components (12, 50) (e.g., as in the alternative embodiment of FIGS. 13-31).

Figure 6A:
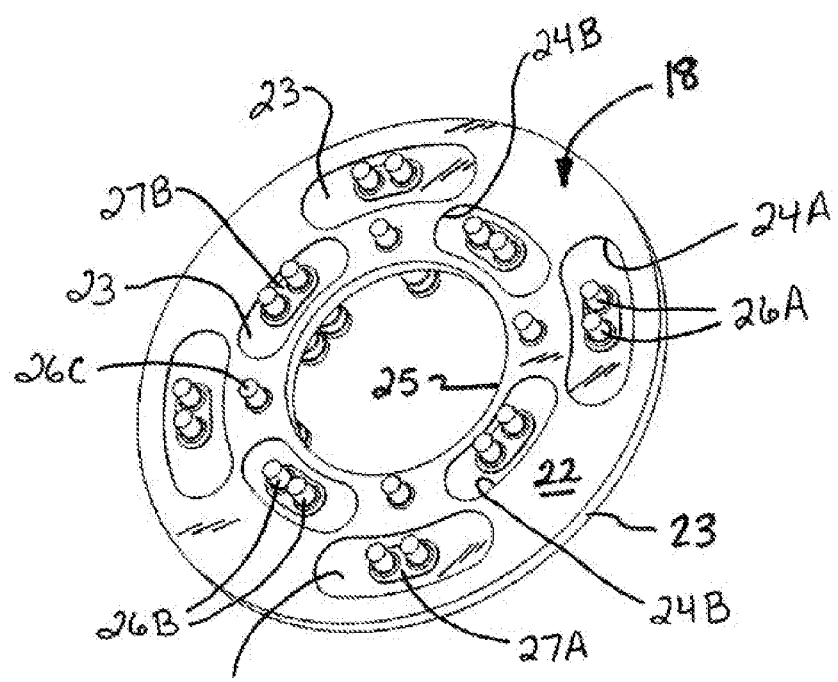
FIG. 6A is a perspective view of the proximal side of the signal interface adapter of the system of FIG. 4, with the housing removed.
Figure 6B:
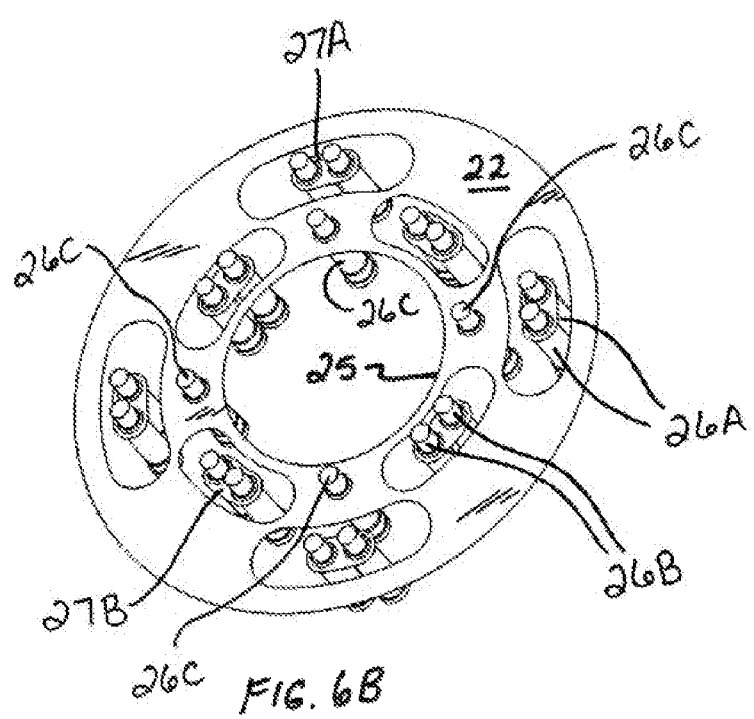
FIG. 6B is the same view as FIG. 6A, but with the cover plate removed.
Figure 7A:
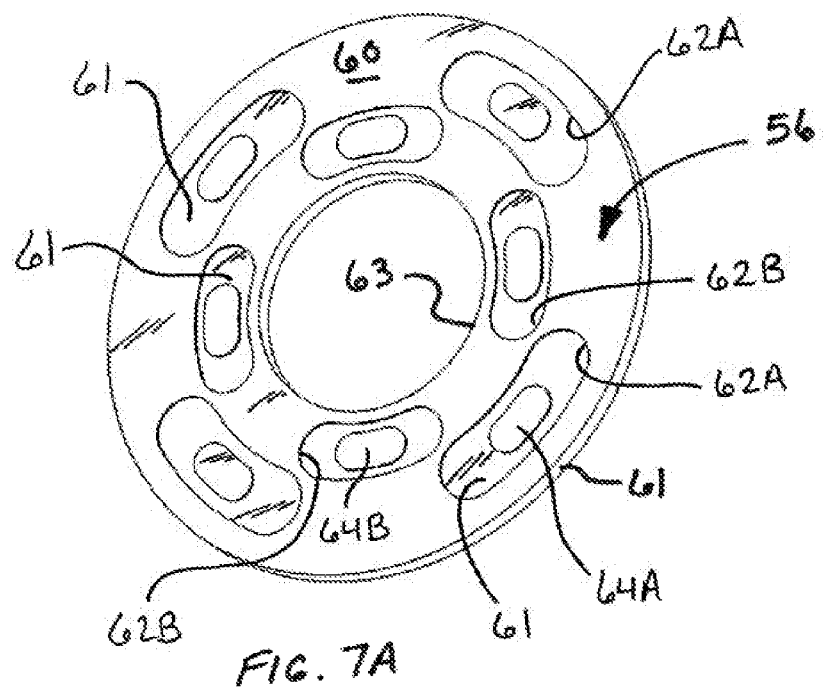
FIG. 7A is a perspective view of the distal side of the instrument connector of the system of FIG. 4, with the housing removed.
Figure 7B:
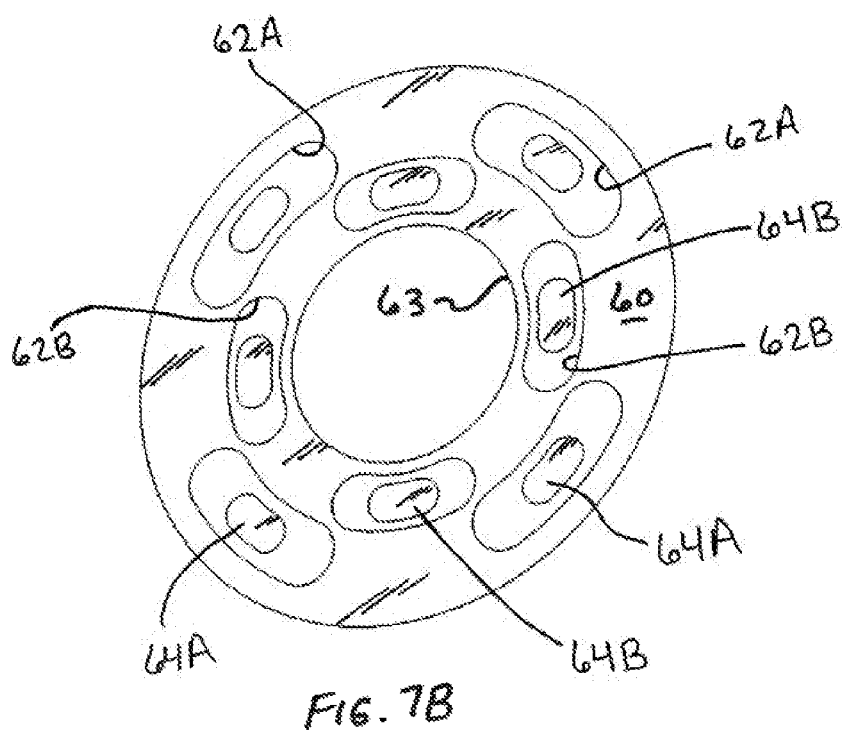
FIG. 7B is the same view as FIG. 7A, but with the cover plate removed.

Each conductive ring (22, 60) is mounted on an insulating, annular cover plate (23, 61), wherein the cover plate is absent in FIGS. 6B and 7B. Each conductive ring (22, 60) includes a plurality of circumferentially arranged and spaced-apart curved oval apertures (24A, 24B, 62A, 62B), arranged in a pair of concentric, spaced-apart bands. Thus, conductive ring (22) of signal interface adapter (12) has an outer band of spaced-apart curved oval apertures (24A), and an inner band of spaced-apart curved oval apertures (24B), arranged about a central aperture (25). Similarly, conductive ring (60) of instrument connector (50) has an outer band of spaced-apart curved oval apertures (62A), and an inner band of spaced-apart curved oval apertures (62B), arranged about a central aperture (63). Conductive oval islands (27A, 27B, 64A, 64B) are located within the curved oval apertures (24A, 24B, 62A, 62B), electrically isolated from the rest of the conductive ring (22, 60). Thus, the conductive oval islands (27A, 27B, 64A, 64B) are smaller than the curved oval apertures (24A, 24B, 62A, 62B) in which they are located. As explained below, each of the conductive oval islands (64A, 64B) located within the apertures (62A, 62B) in conductive ring (60) of the instrument connector (50) provides a conductive contact that, when the components (12, 50) are in mating engagement, will be in conductive engagement (i.e., conductive contact) with a predetermined pair of pogo pins on the interface adapter (12). In other words, each of the eight oval islands (64A, 64B) provides an electrical contact. As further explained below, the conductive ring (60) provides a ninth electrical contact on the instrument connector (50).

The conductive rings (22, 60), also referred to as guard rings, surround all of the conductive oval islands (27A, 27B, 64A, 64B). Thus, any stray electrical current from one of the oval islands (27A, 27B, 64A, 64B) would first have to cross the guard ring (22, 60) in order to create an electrocution hazard for the patient or the medical practitioner. However, when the components (12, 50) are in mating engagement, the guard rings (22, 60) are not only in electrical communication with each other, but also with an external electrical device (e.g., a generator) operatively connected to the signal interface adapter (via main cable (14)). Thus, the external electrical device can detect stray electrical current jumping from one of the contacts (27A, 27B, 64A, 64B) to the guard ring (22, 60), and immediately shut down the delivery of current to the signal interface adapter.

A plurality of pogo pins (26A, 26B, 26C) (also known as spring pins or spring-loaded contacts) are mounted on the signal interface adapter (12), as seen in FIGS. 5, 6A and 6B. The pogo pins are mounted such that the spring-biased plunger portions thereof extend away from the proximal face (18) of the interface adapter (12). In the exemplary arrangement shown, a pair of pogo pins (26A) are secured within each of the outer oval apertures (24A), and a pair of pogo pins (26B) are secured within each of the inner oval apertures (24A). Each such pair of pogo pins extends through apertures provided in one of the conductive oval islands (27A, 27B). The oval islands (27A, 27B) aid in the proper alignment of each pair of pogo pins, and also provide electrical continuity between the pogo pins of each pair. It will be understood, however, that a single pogo pin can instead be provided within each of the oval apertures, with or without the conductive oval islands (27A, 27B). An additional set of individual pogo pins (26C) is provided. However, rather than being in a paired relationship with an immediately adjacent pogo pin, the individual pogo pins (26C) are arrayed about the interface adapter such that one of these additional pogo pins (26C) is located in the regions between each pair of adjacent oval apertures (24B) of the inner band. Each individual polo pin (26C) extends through an aperture in the conductive ring (22), and is also in conductive contact with the conductive ring (22).

Each of the eight pairs of pogo pins (26A, 26B) provides a conductive contact that, when the components (12, 50) are in mating engagement, will be in conductive engagement with a predetermined one of the conductive oval islands (64A, 64B) on the distal face (56) of the instrument connector (50). The non-paired pogo pins (26C) together provide a ninth conductive contact that, when the components (12, 50) are in mating engagement, will be in conductive engagement with portions of the conductive ring (60) of the instrument connector (50) located between the oval apertures (62B) thereof.

Figure 8:
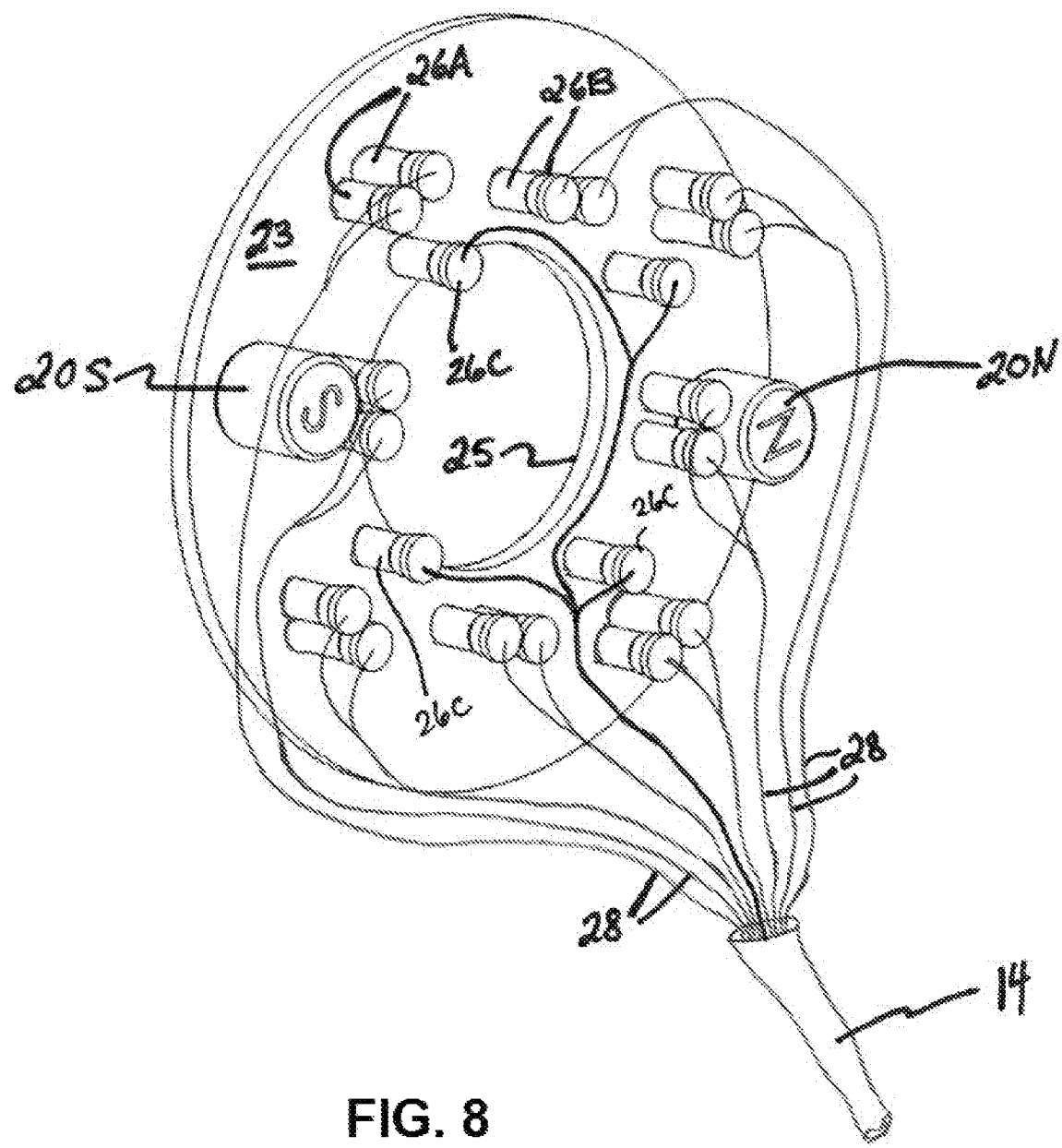
FIG. 8 is a schematic view of the distal side of the signal interface adapter of the system of FIG. 4, with the housing removed, showing the electrical connections to the pogo pin contacts and the wire conduits of the cable of the signal interface adapter.

FIG. 8 depicts a schematic illustration of the internal wiring of the signal interface adapter (12), wherein the housing (13) has been removed. The pogo pins (26A, 26B) of each of the eight pairs are in electrical communication with each other as well as an electrical conductor (e.g., a conductive wire) (28) of main cable (14). The four non-paired pogo pins (26C) are also in electrical communication with each other as well as a ninth electrical conductor (28) of the main cable (14). The electrical communication between the pogo pins (26A, 26B, 26C) and the nine electrical conductors (28) of the main cable (14) can be direct (as shown), or indirect via one or more suitable connectors (and, in some instances, other conductive components). For example, a male or female electrical plug or connector can be provided on the housing (13) of the signal interface adapter (12), with each contact of the plug/connector in electrical communication with a pair of the pogo pins (or the individual pins (26C), and a corresponding mating female or male electrical plug/connector provided on an end of the main cable (14) for operative engagement with the plug/connector on the interface adapter (12).

A similar arrangement is provided in the instrument connector (50), with nine electrical conductors (e.g., wires) of the cable (52) in electrical communication with (directly or indirectly) the conductive oval islands (64A, 64B) and the conductive ring (60). One conductor is in electrical communication with each of the conductive islands (64A, 64B) and a ninth conductor is in electrical communication with the conductive ring (60).

In alternative embodiments, conductive ring (22) and cover plate (23) of the interface adapter (12) are in the form of a printed circuit board ("PCB"). Similarly, conductive ring (60) and cover plate (61) of the instrument connector (50) are also in the form of a PCB. In this arrangement, the conductive islands (27A, 27B, 64A, 64B) as well as the conductive rings (22, 60) are provided by a copper layer patterned on an underlying substrate, wherein the substrate provides the cover plates (23, 61). Instead of wires, conductive traces are provided on the underside of the substrates (cover plates), along with a suitable connection to the cables (14, 52).

The modular signal interface system described herein can be used in a variety of medical, particularly surgical, procedures. A trocar, with or without the signal interface adapter (12) provided thereon, is inserted into a patient in the usual manner, and the obturator removed from the cannula (87). If not already provided on the trocar, the signal interface adapter is attached to the trocar cannula housing (86). Next, a signal-associated surgical instrument such as electrosurgical cutter/stapler (90) having the instrument connector (50) mounted on the shaft thereof is inserted into the trocar.

Specifically, the instrument shaft (92) is inserted into the cannula through the central aperture (19) of the signal interface adapter (12) (FIG. 1). As the instrument shaft (92) is advanced further into the cannula (87), the interface adapter (12) and instrument connector (50) will eventually become sufficiently close so that magnetic forces will pull the instrument connector (50) towards the interface adapter (12), with the instrument connector sliding along the instrument shaft (92). The arrangement of the magnetic regions will also induce torque, causing the instrument connector (50) to rotate about the shaft (92), as necessary, until the instrument connector (50) is in proper rotational alignment with the interface adapter (12) (i.e., with the respective electrical contacts of each component in the desired alignment with the contacts on the other component). The instrument connector (50) will be pulled into engagement with the interface adapter (12) such that each of the conductive islands (64A, 64B) on the distal face of the instrument connector will conductively contact a predetermined pair of the pogo pins (26A, 26B) extending from the proximal face (18) of the interface adapter (12). In addition, the conductive ring (60) will conductively contact the four non-paired pogo pins (26C).

The spring-biased nature of the pogo pins (26A, 26B, 26C) facilitates sufficient contact for providing electrical conductivity, particularly since manufacturing tolerances can be such that intimate contact may not be guaranteed if conductive islands (without pogo pins) are employed as the electrical contacts for the signal interface adapter (12). Nevertheless, the pogo pins (26A, 26B, 26C) are mounted on the interface adapter (12) such that the magnetic engagement of the two components (12, 50) causes the plunger portion of each pogo pin to be urged inwardly (i.e., into the housing (13)) until the conductive rings (22, 60) of the two components (12, 50) are in contact with each other. As a result, up to nine communication channels are established between the signal interface adapter (12) and the instrument (90), allowing signals (power and/or communication signals) to be transmitted between one or more devices in communication with main cable (14) (e.g., a generator) and the surgical instrument (90).

In addition to providing one of the communication channels, the conductive rings (22, 60) also provide an added safety feature. In order for electrical current to improperly pass from one signal line (i.e., channel) to another signal line (i.e. short out), or to short to the instrument, patient, and/or user, such stray electrical current will first have to travel across one of the conductive rings (22, 60). This feature is a result of the conductive rings (22, 60) surrounding the other electrical contacts (26A, 26B, 64A, 64B) (apart from the non-paired pogo pins (26C) that are functionally part of the contact provided by conductive ring (22)). The ninth communication channel provided by the conductive rings (22, 60), also referred to as the "sense line," can be monitored for any stray current or voltage. If anything is sensed on this sense line, a fault has been detected and power is shut down. Signal line sensing can be done, for example, within the signal interface adapter (12) itself or by the external device (e.g., a generator).

It will be understood that, although the embodiment of FIGS. 1-8 has been shown and described as having conductive islands on the instrument connector (50) and corresponding pogo pins on the signal interface adapter (12), this configuration can be reversed if desired.

FIGS. 9-12 depict an alternative embodiment of a modular signal interface system (110) comprising a signal interface adapter (112) and an instrument connector (150) configured similar to the embodiment of FIGS. 1-8. In this embodiment, however, single pogo pins (126A, 126B) are provided for individual mating engagement with each of the conductive islands (164A, 164B), rather than pairs of pins as in the previous embodiment. In addition, the conductive ring has been omitted from the signal interface adapter (112), as the pogo pins (126C) will provide sufficient contact with the conductive ring (160) of the instrument connector (150). Thus, the pogo pins (126A, 126B, 126C) extend through apertures in the insulating cover plate (123), which is affixed to the housing (113).

During mating engagement of the components (112, 150), the proximal face of the signal interface adapter (112) will often come into contact with the distal face of the instrument connector (150) before the instrument connector (150) has rotated about the instrument shaft into proper alignment. When this occurs in the embodiment of FIGS. 1-8, the exposed ends of the pogo pins will slide across the proximal face of the signal interface adapter as the instrument connector rotates into position. Depending on the amount of rotation necessary for alignment, one or more of the pogo pins may even briefly come into contact with the wrong island contacts (64A, 64B).

In order to prevent such non-mating contact, as well as to facilitate rotational sliding of the instrument connector across the proximal face of the signal interface adapter, the embodiment of FIGS. 9-12 further includes a pair of projections (130) on the distal face of the interface adapter that are received in corresponding recesses (166) on the instrument connector when the two components (112, 150) are in mating engagement with one another. Portions of the projections (130) extend above the exposed ends of the pogo pins, thereby preventing the pogo pins from contacting any portion of the instrument connector (150) until the instrument connector is in proper rotational alignment with the signal interface adapter (112). When proper rotational alignment is achieved, the projections (130) are received within the recesses (166) on the instrument connector (150), and the instrument connector is pulled into mating contact with the interface adapter such that the pogo pins are in electrical contact with the proper conductive islands (i.e., contacts) and conductive ring of the instrument connector. It will be understood that the projections can be provided on either the proximal face of the signal interface adapter or the distal face of the instrument connector, with corresponding recesses for receiving the projections provided on the mating face of the other component. In some embodiments, the projections are formed of a non-conductive material (e.g., plastic).

Projections (130) and recesses (166) for receiving the projections can have any of a variety of configurations, such as captive ball bearings (e.g., ruby ball bearings) rotatingly mounted in the proximal face of the interface adapter and correspondingly shaped recesses in the distal face of the instrument connector. In the embodiment shown in FIGS. 9-12, however, each projection (130) comprises a wheel (131) rotatingly mounted in a frame (132) affixed to the cover plate (123) of the interface adapter (112). Each wheel (131) is mounted in its respective frame (132) such that the rotational axis of the wheel (i.e., the wheel axle) extends radially away from the central aperture (119) of the interface adapter (112).

Figure 9:
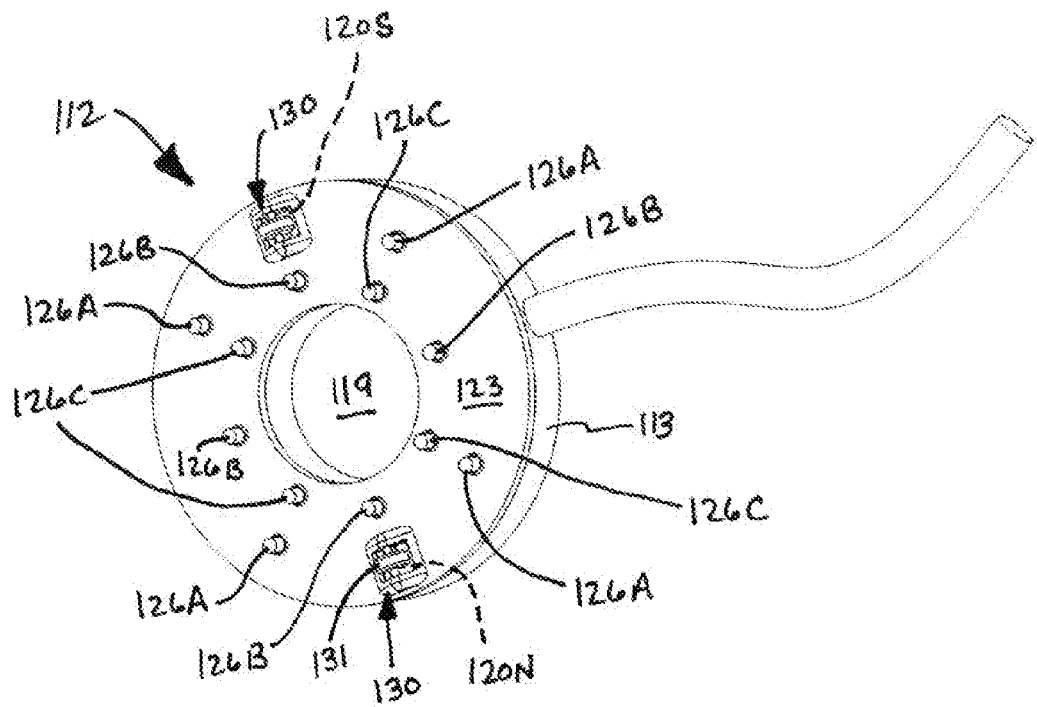
Figure 10:
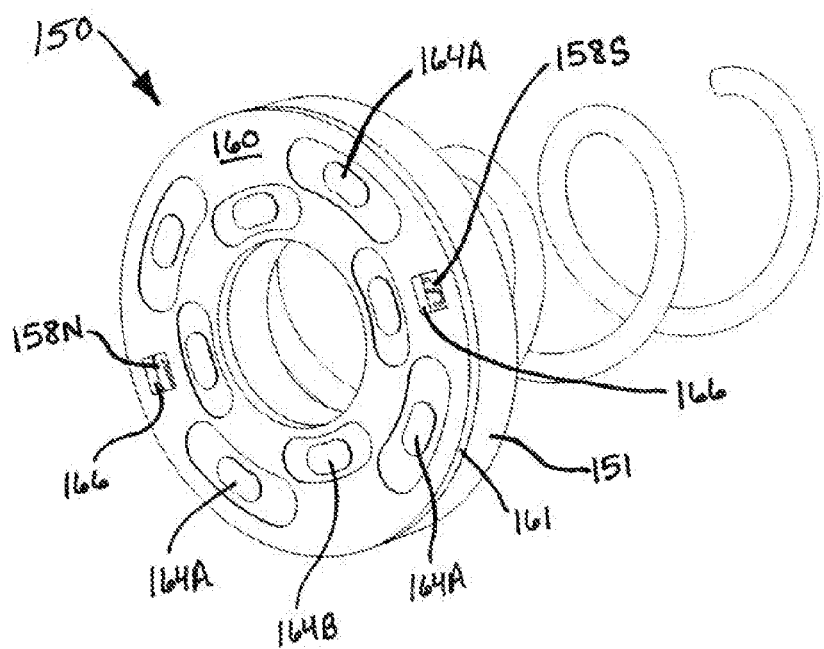
Figure 11:
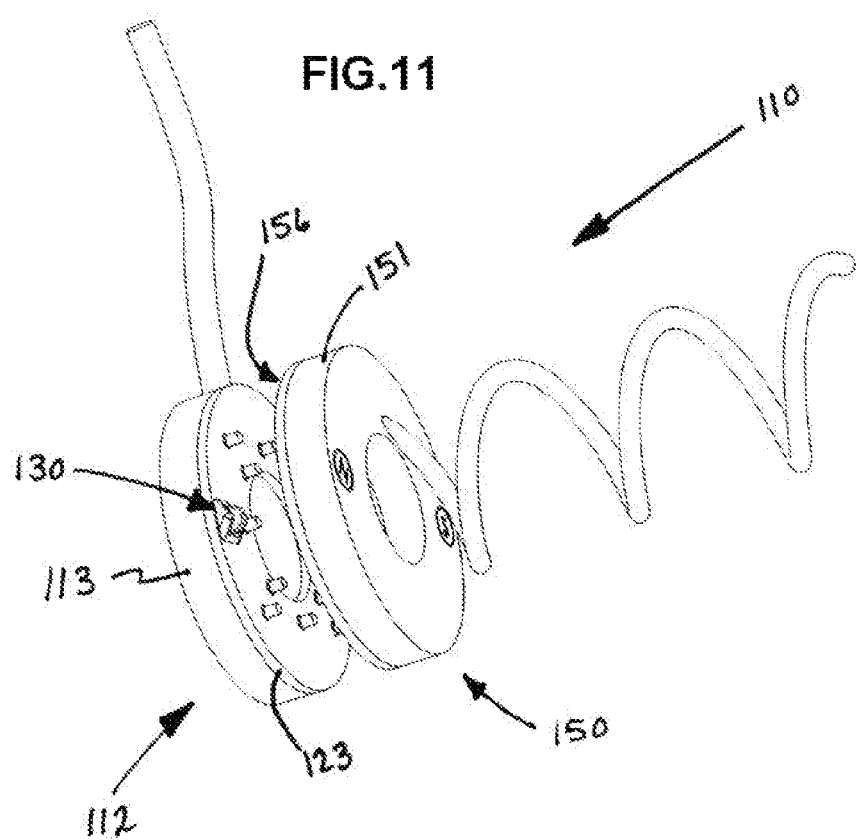
FIG. 11 is a perspective view of the modular signal interface system of FIG. 10.
Figure 12:
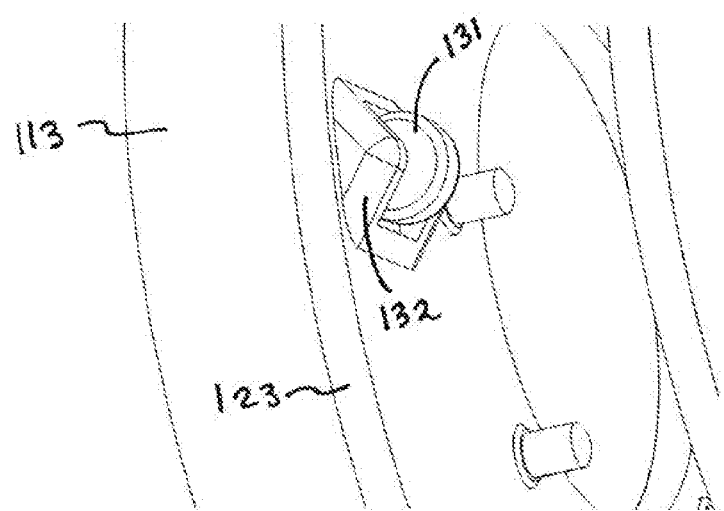
FIG. 12 is an enlarged view of a portion of FIG. 11.

As also shown in FIG. 9, the magnets (120N, 120S) of the signal interface adapter (112) are located directly beneath the projections (130), within the housing (113). On the instrument connector (150), rectangular recesses (166) are provided in the conductive ring (160) and cover plate (161), and are sized, configured and located so as to receive the wheels (131) and frames (132) of the projections (130) when the components (112, 150) are in mating engagement. As depicted in FIG. 10, magnets (158N, 158S) are located at the base of the recesses (166), within the housing (151) of the instrument connector (150). Of course other forms of recesses (166) can be provided, depending in part on the size and shape of the projections (130). In general, recesses (166) are sized and configured to allow the projections (130) to drop into the recesses a sufficient depth so that the desired conductive engagement is made between the contacts on the two components (112, 150). In this embodiment, since the proximal face of the cover plate (123) of the interface adapter (112) is non-conductive (i.e., does not provide one of the conductive contacts), mating engagement of the two components (112, 150) does not necessarily require contact between the proximal face of the cover plate (123) of the interface adapter and the distal face (156) of the instrument connector. However, recesses (160) can be configured to be sufficiently deep in order to fully receive projections (130) therein—i.e., until contact between the proximal face of the cover plate (123) of the interface adapter and the distal face (156) of the instrument connector is achieved, thereby assuring that proper mating engagement is maintained throughout use of the instrument and providing audible and tactile indications of engagement.

As the instrument connector (150) rotates into proper alignment with the interface adapter under the influence of the magnets, the distal face (156) of the instrument connector (150) will ride atop the wheels (131) until the wheels drop into the recesses (166). Not only does this bring the opposing magnets into closer proximity to one another, thus increasing the force that holds the components (112, 150) in mating engagement, it will also provide an audible click and a tactile indication that mating engagement has been achieved. It will be understood, of course, that just like the pogo pins can be provided on the instrument connector rather than the interface adapter, the projections (130) can be provided on the instrument connector rather than (or in addition to) the interface adapter along with corresponding recesses on the interface adapter. It will also be understood that various other forms of projections may be provided on either or both components (112, 150), including non-rotating projections that will nevertheless slide along the opposing face of the other component until received in an appropriately shaped recess when proper alignment is achieved.

FIGS. 13-31 depict yet another alternative embodiment of a modular signal interface system (210) comprising a signal interface adapter (212) and an instrument connector (250) configured similar to the previously described embodiments. In this embodiment, however, pogo pins or other pin-type contacts are not used on either component (212, 250). Instead, planar, mating contacts are provided on each face of the components (212, 250), similar to those described above with respect to the instrument connector (50, 150). In addition, the signal interface adapter (212) is configured to be removably mounted on the proximal end of a trocar cannula housing (e.g., trocar cannula housing (86) in FIG. 1).

Figure 13:
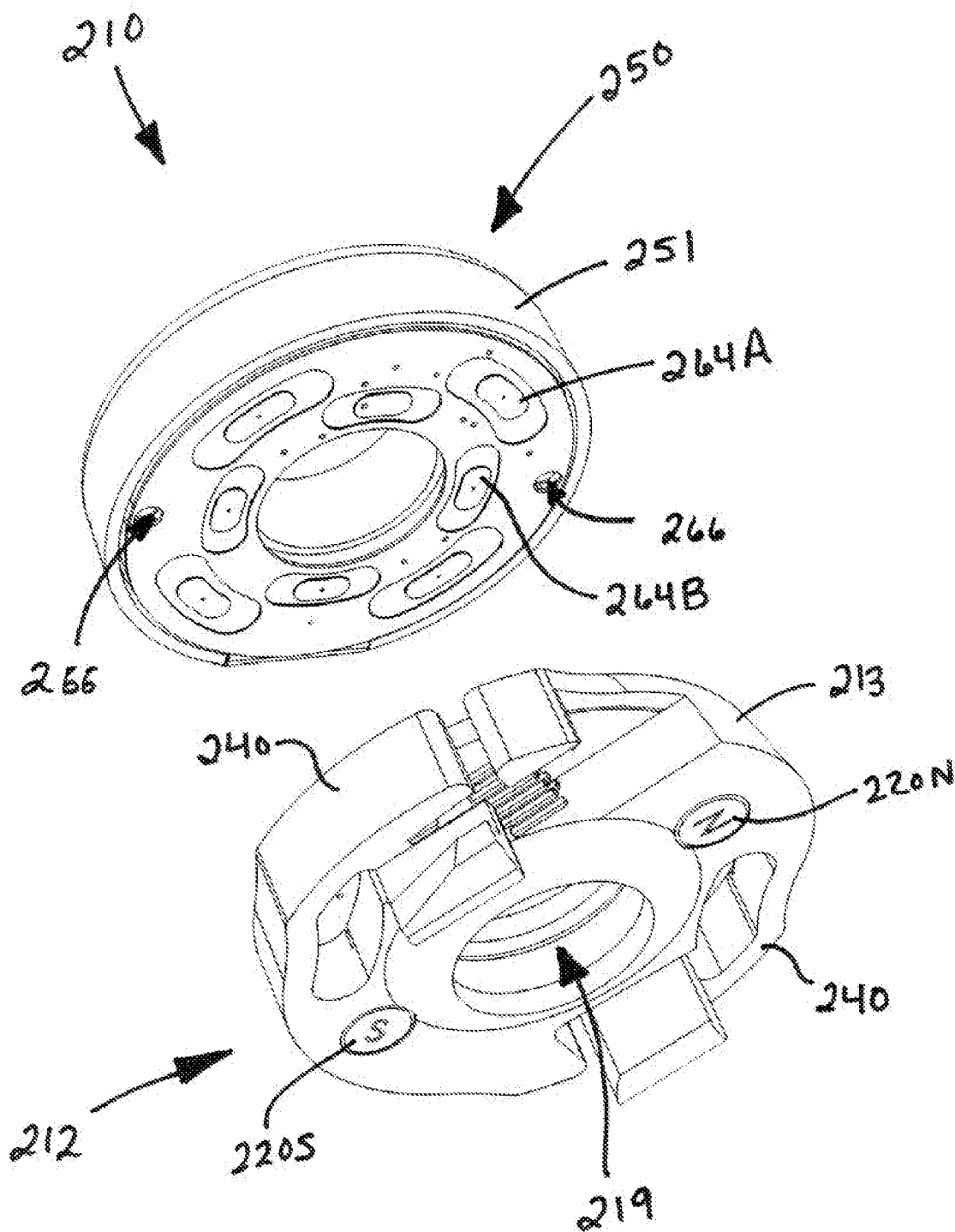
Figure 14:
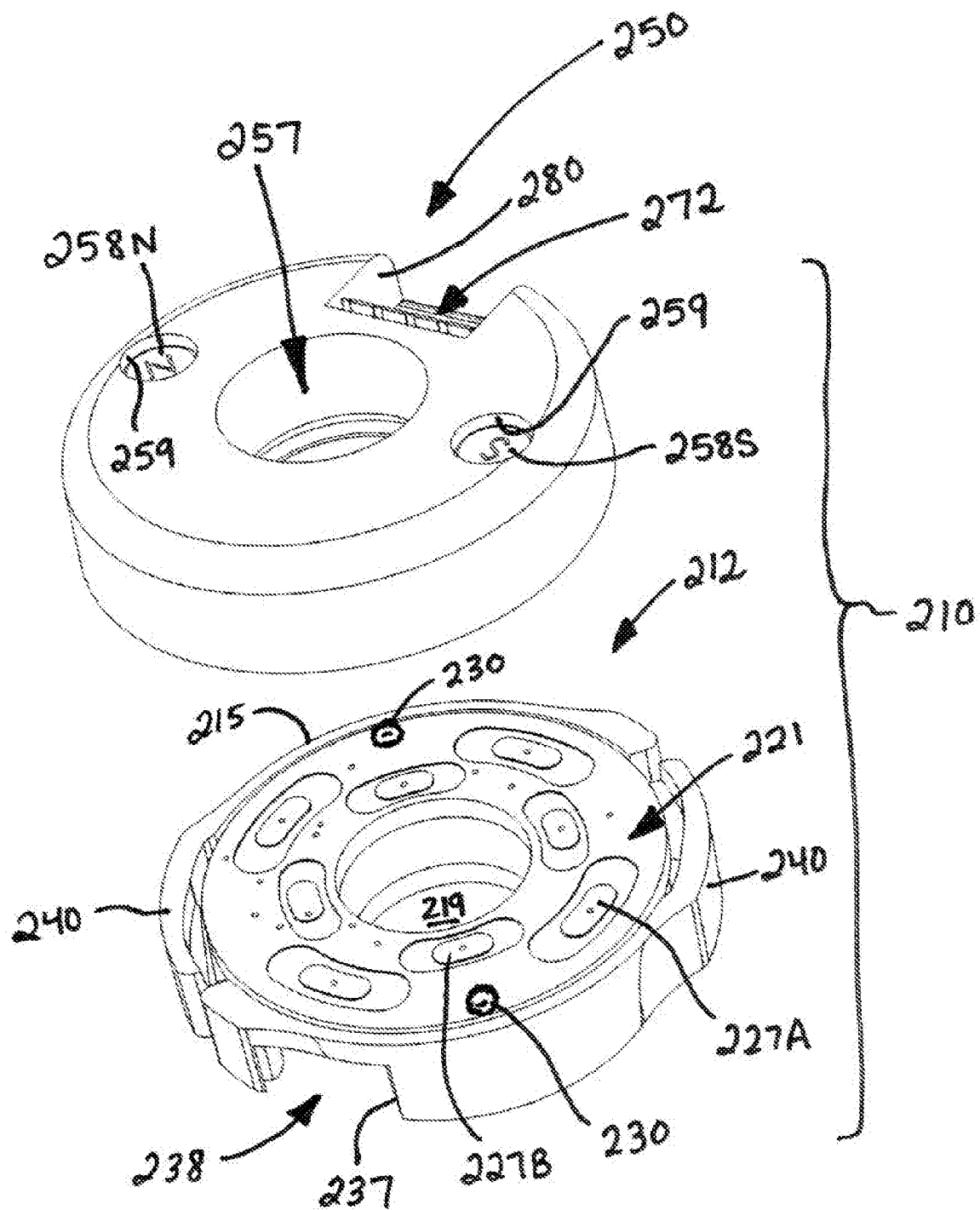
Figure 15:
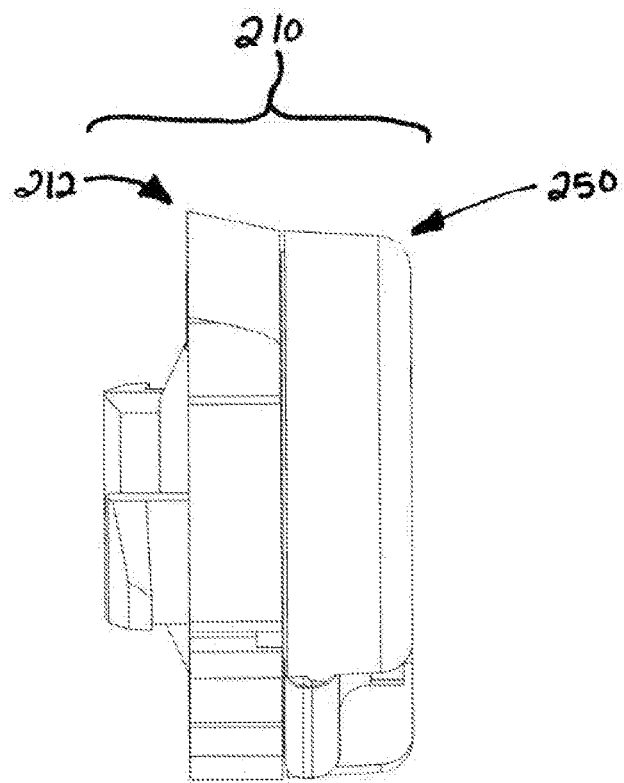
FIG. 15 is a side view of the modular signal interface system of FIG. 13, depicting the signal interface adapter and instrument connector thereof in mating engagement.

FIGS. 13 and 14 are perspective views of modular signal interface system (210), wherein the signal interface adapter (212) and instrument connector (250) are shown disengaged from one another. FIG. 13 depicts the distal faces of the two components (212, 250), while FIG. 14 depicts the proximal faces of the two components (212, 250). FIG. 15 is a side view that depicts the two components (212, 250) in mating engagement. It will be understood that the cable extending from the interface adapter (212) to an external electrical device, as well as the cable extending from the instrument connector (250) to a signal-associated instrument have been omitted in FIGS. 13-31. However, exemplary connectors for such cables are shown, and are further described below.

Like the previously described embodiments, the signal interface adapter (212) is configured to be mounted on the proximal end of a trocar cannula housing having a cannula extending distally therefrom, and the instrument connector (250) is configured to be slidingly mounted on the shaft of a surgical instrument (e.g., as shown in FIG. 1). As before, each of the interface adapter (212) and the instrument connector (250) are annular in shape, having central apertures (219, 257) extending therethrough. When the two components (212, 250) are in mating engagement with one another (FIG. 15), the apertures (219, 257) are axially aligned with one another such that a constant diameter cylindrical opening extends therethrough. The apertures (219, 257) are sized and configured to slidably and rotatably receive an instrument shaft therethrough. As before, it will also be understood that the shape of interface adapter (212) and instrument connector (250) shown in FIGS. 13-31 is merely exemplary.

The signal interface adapter (212) generally comprises a housing (213) and a cover plate (221) mounted thereto. In this embodiment, cover plate (221) is in the form of a PCB having a patterned, conductive ring (222) on the proximal side of a substrate (223). PCB cover plate (221) is multi-layered, with plated through-holes (or vias) (234) connecting portions of the conductive ring (222) to underlying layers that include various electrical traces (not shown).

The proximal side of housing (213) is generally cup-shaped, having an outer rim (215) with an inner diameter slightly larger than the outer diameter of PCB cover plate (221). PCB cover plate (221) is received in the proximal side of housing (213), on proximal surface (217) of housing (213), within rim (215) (see FIG. 19). PCB cover plate (221) can be secured in place by an adhesive, mechanical fasteners such as screws or rivets, and/or press fitting.

As in the previously described embodiments, a pair of opposite polarity magnets (220N, 220S) are provided on signal interface adapter (212). Similarly, a pair of opposite polarity magnets (258N, 258S) are provided on instrument connector (250). Once again the opposite polarity magnets of each component (212, 250) of the interface system are located 180 degrees apart (i.e., on opposite sides of the central apertures (219, 257)). A pair of cylindrical bores (233) extend through the thickness of housing (213) between proximal end surface (217) and distal end surface (229) (see FIGS. 21 and 22). Cylindrical bores (233) receive magnets (220N, 220S) therein, with the magnets held in place by an adhesive, mechanical fasteners, and/or press fitting. On the instrument connector, magnets (258N, 258S) are received in cylindrical cavities (259) that are open at the proximal face (254), and held in place by an adhesive, mechanical fasteners, and/or press fitting (see FIG. 14).

Figure 19:
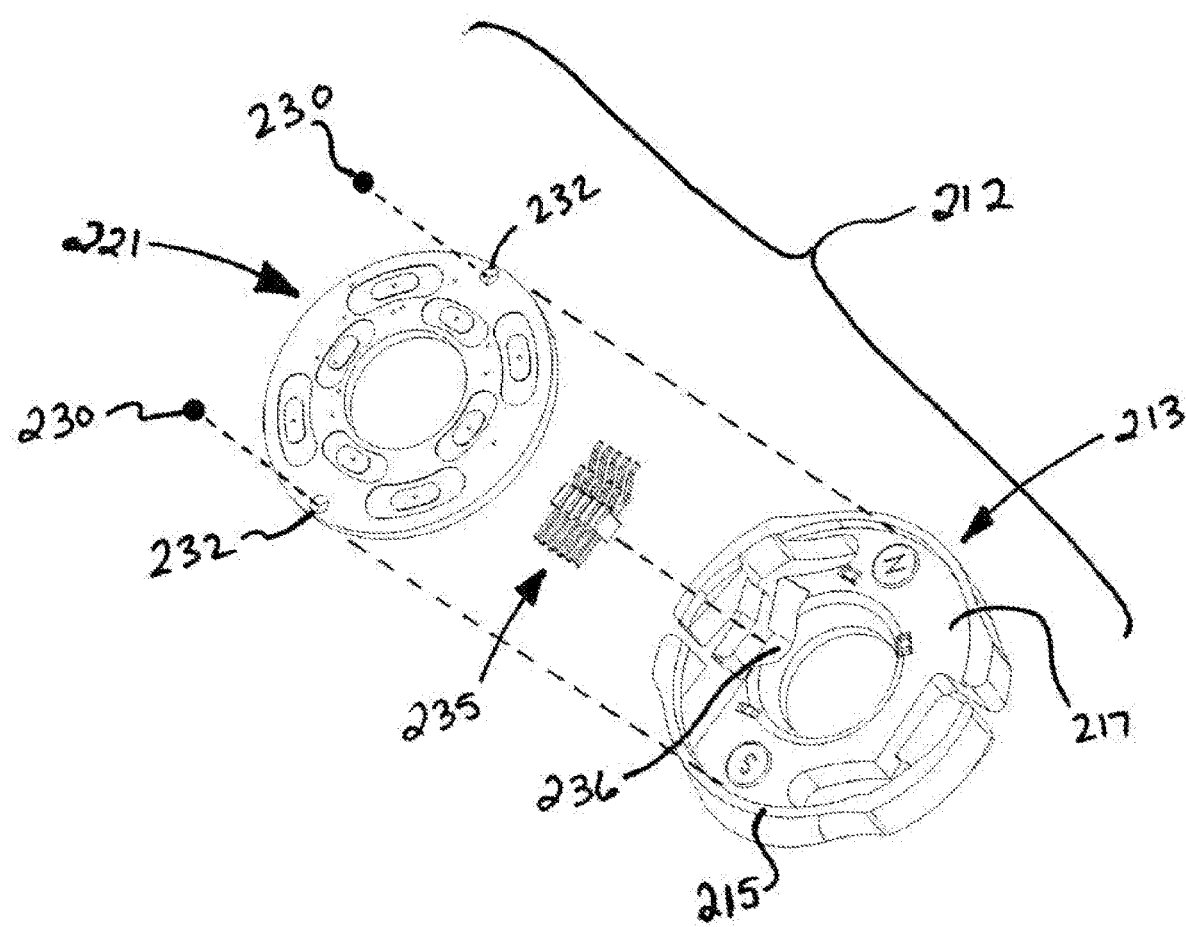
FIG. 19 is an exploded view of the signal interface adapter of FIG. 16, viewed from the proximal side.
Figure 20:
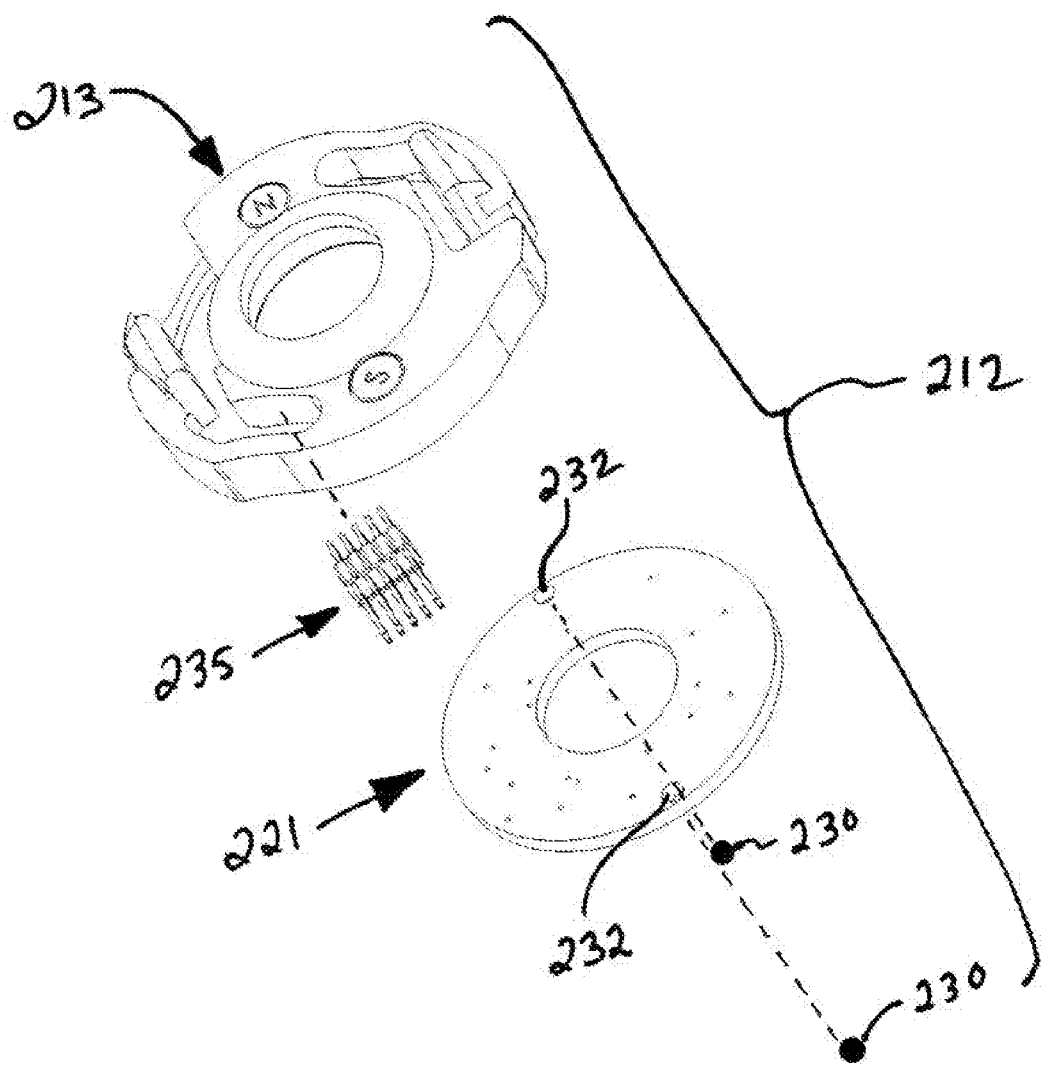
FIG. 20 is an exploded view of the signal interface adapter of FIG. 19, viewed from the distal side.
Figure 21:
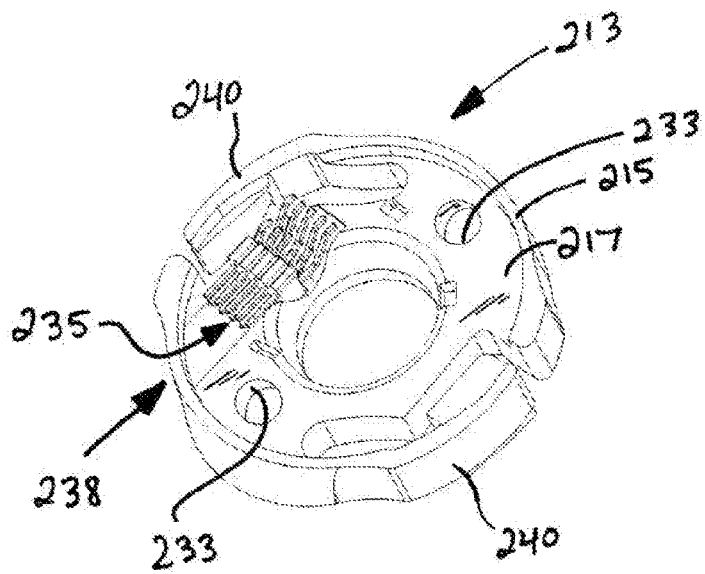
FIG. 21 depicts a perspective view of the housing of the signal interface adapter of FIG. 13.
Figure 22:
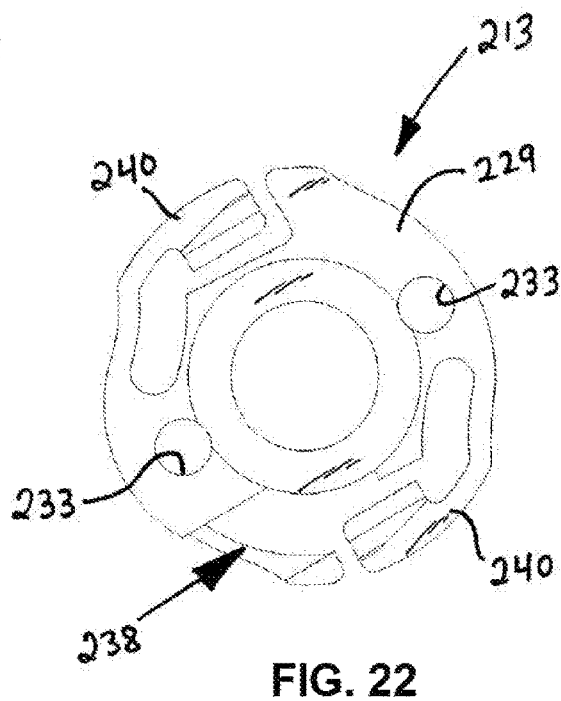
FIG. 22 depicts a bottom (distal) plan view of the signal interface adapter of FIG. 13.
Figure 23:
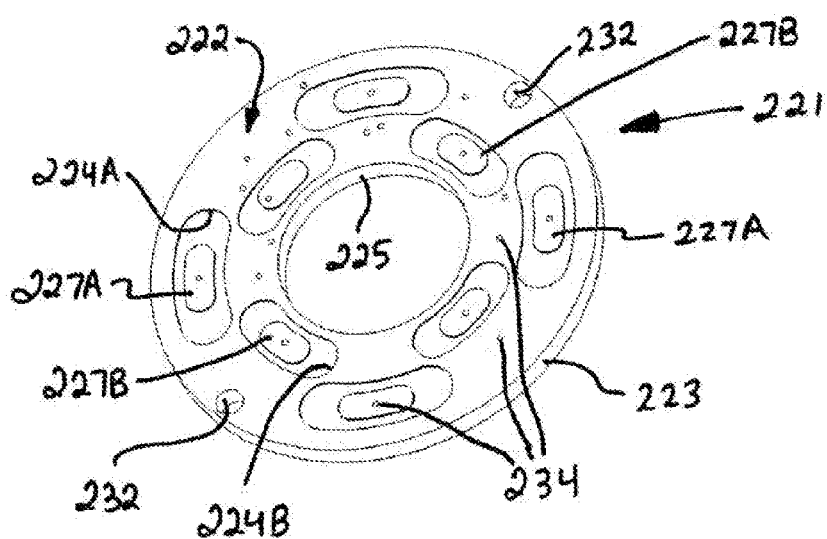
FIG. 23 depicts a perspective view of the proximal side of the PCB cover plate of the signal interface adapter of FIG. 13.
Figure 24:
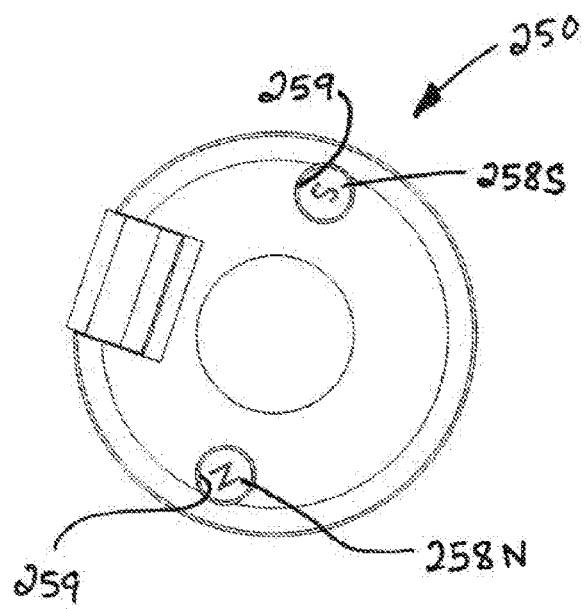
FIG. 24 depicts an upper (proximal) plan view of the instrument connector of the system of FIG. 13.
Figure 25:
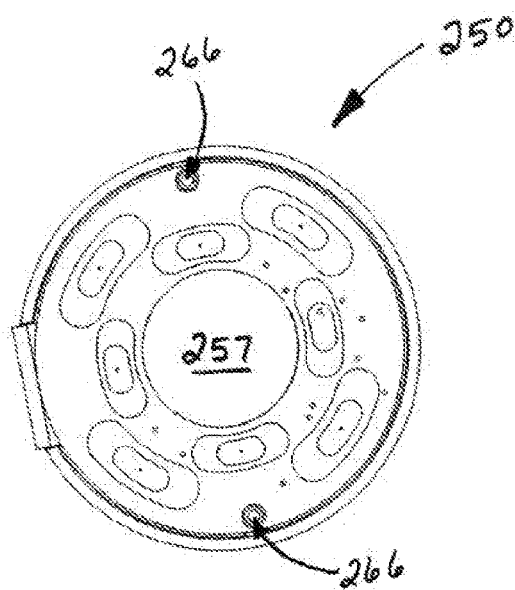
FIG. 25 depicts an bottom (distal) plan view of the instrument connector of FIG. 24.
Figure 26:
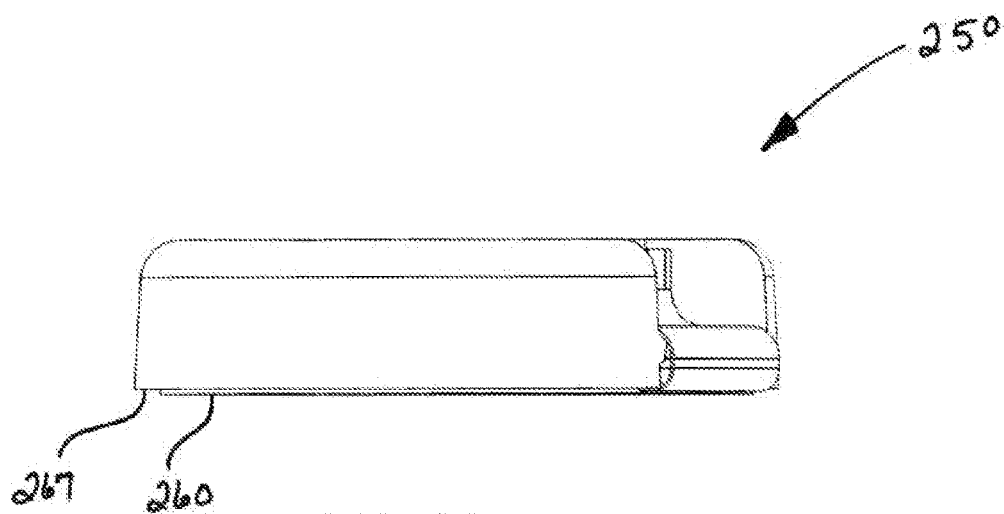
FIG. 26 depicts a side view of the instrument connector of FIG. 24.

A 10-pin electrical connector (235) is received in a recess (236) provided in proximal end surface (217) of housing (213) of the interface adapter (212), beneath the PCB cover plate (221), as best seen in FIGS. 19 and 21. The pins of connector (235) are in electrical communication with the various contacts of the interface adapter (212) using conductive traces and the like (not shown). A rectangular cutout (237) (see FIG. 14) is provided in the sidewall of the housing (213), thus providing a passageway (238) through which a female connector on a cable (not shown) can be operatively attached to the connector (235) in order to provide electrical communication to the external device (similar to main cable (14) described previously).

Figure 16:
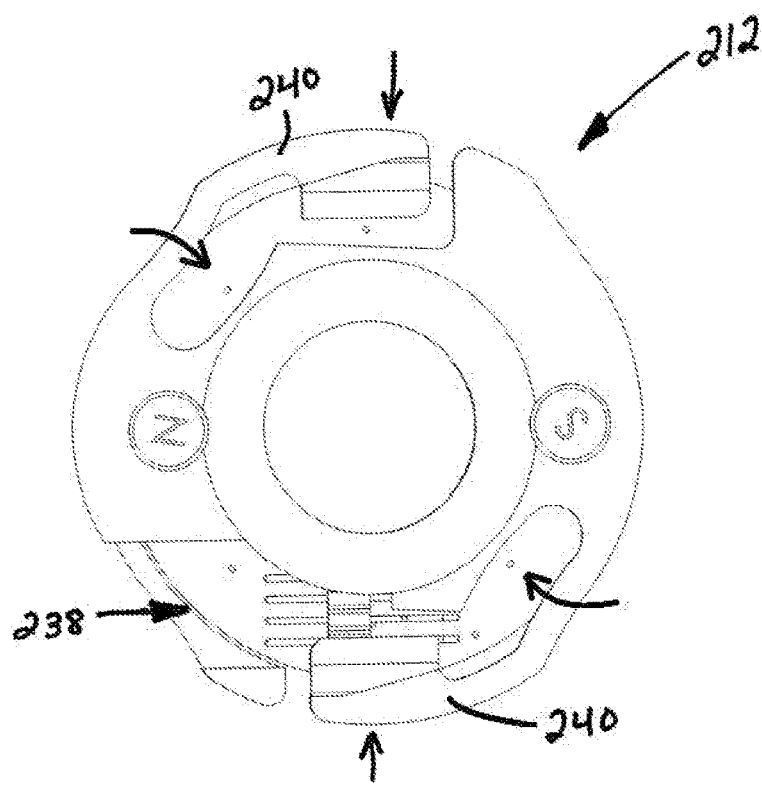
FIG. 16 is a bottom (or distal) end view of the signal interface adapter of the system of FIG. 13.
Figure 17:
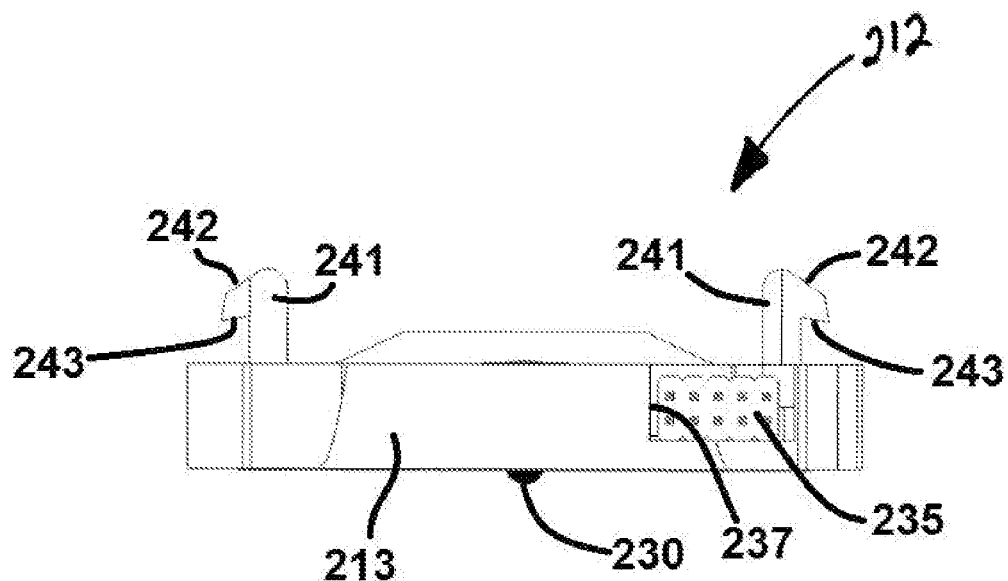
FIG. 17 is a side view of the signal interface adapter of FIG. 16.
Figure 18:
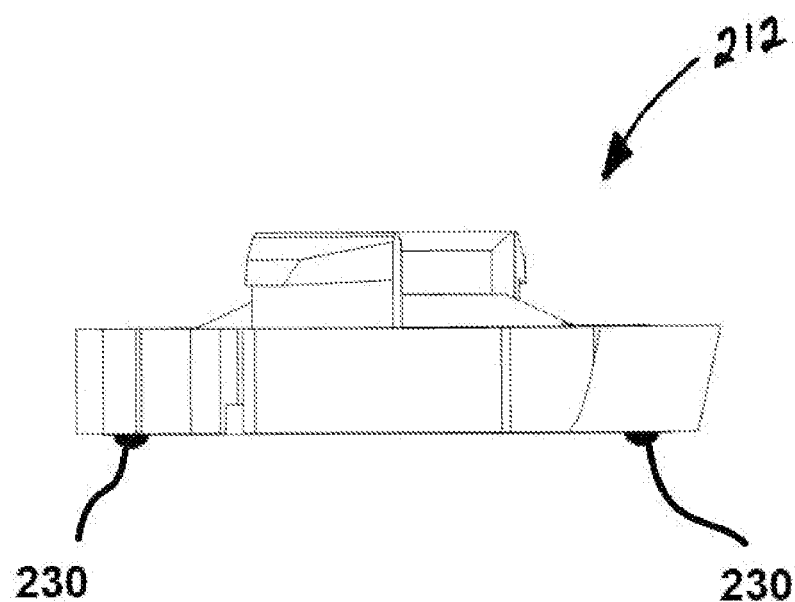
FIG. 18 is a side view of the signal interface adapter of FIG. 17, rotated 90 degrees.

On its distal side, the interface adapter (212) is configured to be removably mounted on the proximal end of a trocar cannula housing (e.g., trocar cannula housing (86) in FIG. 1). In particular, a pair of spring-like cantilevered arms (240) are provided on opposite sides of the housing (213). Cantilevered arms (240) can be flexed radially inward, as shown in FIG. 16. Such resilient flexing is enhanced by forming the housing (213) of a suitable resilient material, such as molded plastic. A distally extending latch arm (241) is provided at the free end of each cantilevered arm (240), and terminates in radially extending clip (242) having a shoulder (243). The clips (242) are located and configured to be lockingly received by correspondingly shaped slots on the proximal end of a trocar cannula housing such that the shoulders (243) can be locked beneath a bottom edge of the slot.

For example, in the embodiment shown clips (242) are configured for locking engagement with slots on the first housing member of the trocar housing shown and described in U.S. Patent Pub. No. 2005/0070947 ("the '947 App.", published on Mar. 31, 2005, and incorporated by reference herein.

In particular, clips (242) cooperate with the first housing member (36 in the '947 App.) in the same manner as the "mating latches 164, 166" are received in the slots on the upper surface of the first housing member (see FIG. 2 of the '947 App.). After the cannula has been inserted into the patient, the obturator assembly is detached from the trocar housing, and the interface adapter (212) shown and described herein is attached to the trocar cannula housing in its place. The clips (242) are inserted into the slots on the trocar cannula housing. The sloped distal surface of the clips (242) will be urged against the sides of the slots, causing the cantilevered arms (240) to flex radially inward. The clips (242) proceed down the slots until their shoulders (243) extend past the base of the slots, resulting in the clips (242) snapping radially outward thus securing the interface adapter (212) to the trocar cannula housing. In order to remove the interface adapter from the trocar housing, the cantilevered arms (240) are pressed radially inward until the shoulders (243) clear the sidewalls at the base of the slots on the cannula housing, allowing the interface adapter to be removed. It will be understood, of course, that the interface adapter (212) can be configured in a variety of other ways to allow for removable mounting to trocar cannula housings of various configurations, whether now known or hereafter developed.

Cover plate (221), comprising a PCB having a patterned, conductive ring (222) on the proximal side of the insulating substrate (223), includes a plurality of conductive contacts. Conductive ring (222) is generally annular in shape, having a central aperture (225) corresponding to the central aperture (219) of the interface adapter (212). While the conductive ring (222) itself provides one contact for mating engagement with a corresponding conductive ring (260) and/or another contact on the instrument connector (250), the PCB cover plate (221) further includes a plurality of circumferentially arranged and spaced-apart contacts in the form of conductive oval islands (227A, 227B) arranged in a pair of concentric, spaced-apart bands, similar to the previous embodiments. Thus, the PCB cover plate (221) further includes an outer band of spaced-apart contacts (227A), and an inner band of spaced-apart contacts (227B), arranged about a central aperture (225). The conductive oval islands, i.e., the contacts (227A, 27B) are once again located within curved oval apertures (224A, 224B) provided in the conductive ring (222), such that the contacts (227A, 227B) are electrically isolated from the conductive ring (222) that surrounds each of the contacts (227A, 227B).

Like the embodiment of FIGS. 9-12, the interface adapter (212) includes a pair of projections (230) that are received in corresponding recesses (266) on the instrument connector (250) when the two components (212, 250) are in mating engagement with one another. As before, the projections (230) alternatively can be provided on the instrument connector (250) with corresponding recesses (266) provided on the interface adapter (212). In this embodiment, the projections comprise captive ball bearings (e.g., non-conductive ruby ball bearings) that not only prevent non-mating electrical contact prior to proper alignment of the components (212, 250), but also facilitate rotational sliding of the instrument connector and the signal interface adapter. The bearings (230) are captively mounted in apertures (232) provided in PCB cover plate (221), such that the bearings (230) can rotate therein. Similar to the projections (130) of the previous embodiment, portions of the bearings (230) extend above the conductive ring (222) and islands (227A, 227B), thereby preventing the conductive ring (222) and islands (227A, 227B) from contacting any portion of the instrument connector (250) until the instrument connector is in proper rotational alignment with the signal interface adapter (212). When proper rotational alignment is achieved, the bearings (230) are received within the recesses (266) on the instrument connector (250), and the instrument connector is pulled into mating contact with the interface adapter. It will be understood, of course, that the bearings (230) (or other projections) can be provided on the instrument connector rather than on (or in addition to) the interface adapter along with corresponding recesses on the interface adapter. Also, while recesses (266) are in the form of cavities provided by apertures (271) in the cover plate (261) of the instrument connector and other underlying features described below, the recesses can be configured in a variety of other ways, depending on the nature of the projections on the interface adapter (212).

Turning to the instrument connector (250) component of the modular interface system (212), this component is configured similar to the interface adapter (212). However, instead of a rigid PCB, instrument connector (250) employs a flexible printed circuit board ("FPCB") for providing the mating contacts. The FPCB allows for the contacts to protrude outwardly and resiliently from the distal face of the instrument connector (250) in order to facilitate mating communication with the contacts on the interface adapter (212). Thus, the contacts provided by the FPCB replace the spring-loaded pogo pins. In addition, an elastomeric sheet located between the FPCB and the instrument connector housing (251) provides support beneath each of the contacts, urging the contacts outwardly in order to facilitate mating contact. It will be understood that both the interface adapter (212) and the instrument connector (250) can employ a FPCB to provide resiliently biased contacts in the manner described below. As yet another alternative, the instrument connector employ a rigid PCB while the interface adapter employs a FPCB so as to provide resiliently biased contacts in the manner described below.

Like the previously described embodiments, the instrument connector (250) is configured to be slidably mounted on an instrument shaft. The instrument shaft is slidingly received through the central aperture (257) of the instrument connector (250) such that the connector can slide axially and rotatingly along at least a portion of the instrument shaft. The instrument connector (250) generally comprises a housing (251) and a FPCB cover plate (261) mounted thereto. FPCB cover plate (261) has a patterned, conductive ring (260) on the proximal side of a flexible, insulating substrate. FPCB (261) is multi-layered, with plated through-holes (or vias) to connect portions of the conductive ring (260) to underlying layers that include various electrical traces (not shown).

Figure 29:
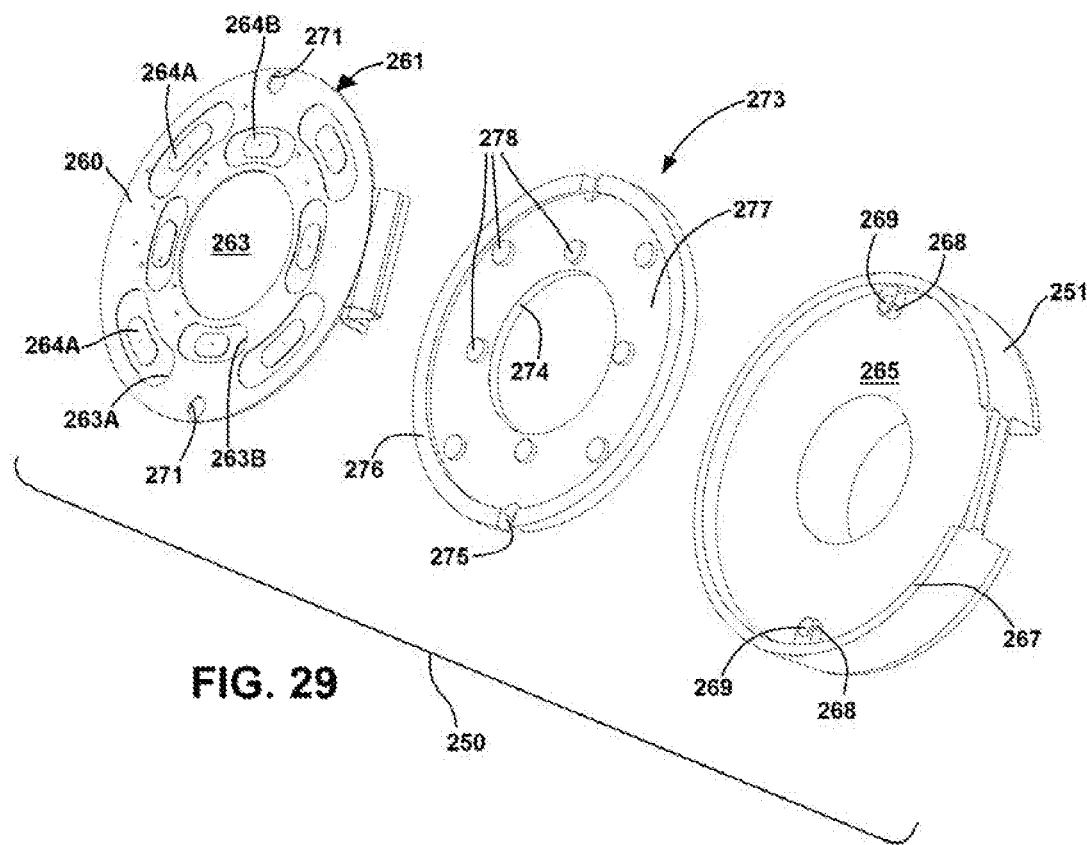
FIG. 29 is an exploded view of the instrument connector of FIG. 24, viewed from the distal side.
Figure 30:
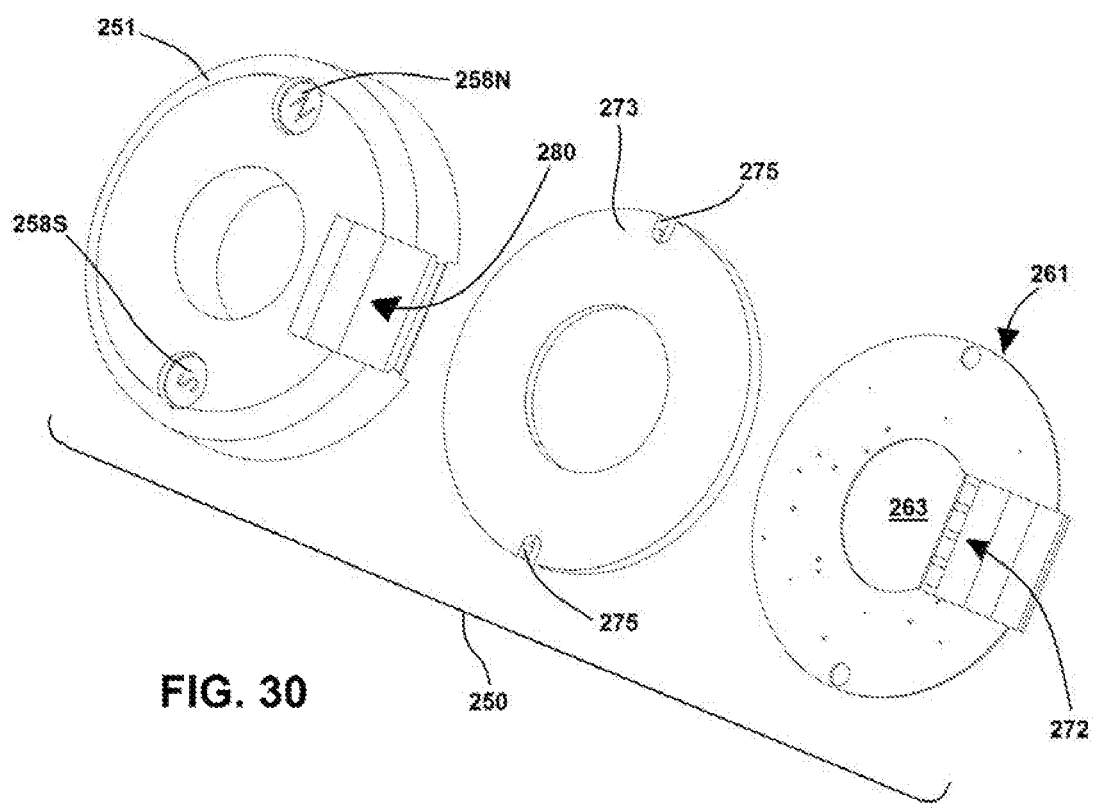
FIG. 30 is an exploded view of the instrument connector of FIG. 29, viewed from the proximal side.

As best seen in FIG. 29, the distal face (265) of the housing (251) is recessed, having an outer rim (267) extending around its perimeter. A pair of arcuate members (268), each having a hemispherical cavity (269) therein, are provided on opposite sides of the distal face (265), extending radially inward from the outer rim (267) as shown. The hemispherical cavities (269) provide the bottom of the recesses (266) for receiving the bearings (230). The members (268) are not as high as the outer rim (267), such that the upper (i.e., distal) surface of each arcuate member (268) does not extend to the upper surface of the outer rim in order to facilitate receiving a portion of one of the bearings (230) in each of the hemispherical cavities (269).

A resilient, elastomeric support member (273) having a central aperture (274) is received on the distal face (265) of the housing (251). The support member (273) includes a pair of cutouts (275) that receive the arcuate members (268) on the distal face (265) of the housing (251) therein. A plurality of contact biasing projections are provided on the support member (273), including a plurality of support nubs (278) that extend away from the distal surface (277) of the support member (273), as well as an outer support rim (276) that extends about the periphery of the support member (273). The support nubs (278) and outer support rim (276) are of approximately the same height with respect to the distal surface (277).

Figure 31:
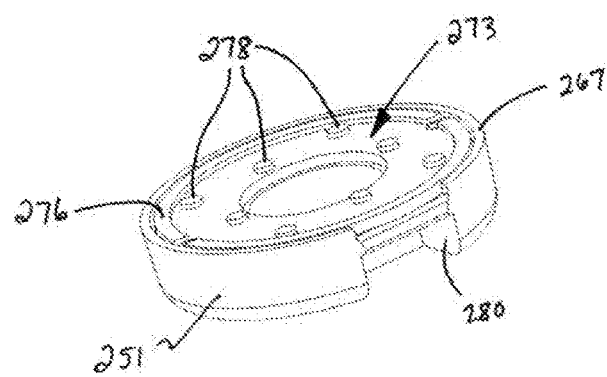
FIG. 31 is a perspective view of the instrument connector of FIG. 24, wherein the FPCB cover plate has been removed.

The support member (273) is received atop the recessed distal face (265) of the housing (251), surrounded by the outer rim (267), with arcuate members (268) positioned within cutouts (275). As best seen in FIG. 31, the support member (273) is configured such that the upper (i.e., distal) surface of the outer support rim (276) and support nubs (278) are generally level with each other and with the upper (distal) surface of the outer rim (267) of the housing (251), and such that there is a small gap between the outer perimeter of support rim (276) and the inner circumference of outer rim (267).

FPCB cover plate (261), comprising a patterned, conductive ring (260) on the distal side of an insulating substrate, includes a plurality of conductive contacts. Conductive ring (260) is generally annular in shape, having a central aperture (263) corresponding to the central aperture (257) of the instrument connector (250). While the conductive ring (260) itself provides one contact for mating engagement with the corresponding ring contact (222) on the signal interface adapter (212), the FPCB cover plate (261) further includes a plurality of circumferentially arranged and spaced-apart contacts in the form of conductive oval islands (264A, 264B) arranged in a pair of concentric, spaced-apart bands. Thus, FPCB cover plate (261) has an outer band of spaced-apart contacts (264A), and an inner band of spaced-apart contacts (264B), arranged about the central aperture (263). The conductive oval islands, i.e., the contacts (264A, 264B) are located within curved oval apertures (263A, 263B) formed in the conductive ring (260), such that the contacts (264A, 264B) are electrically isolated from the rest of the conductive ring (260). FPCB cover plate (261) also includes a pair of apertures (271) located on opposite sides of the cover plate adjacent the outer perimeter, which define the entrance portion of the recesses (266) for receiving the bearings (230).

Figure 27:
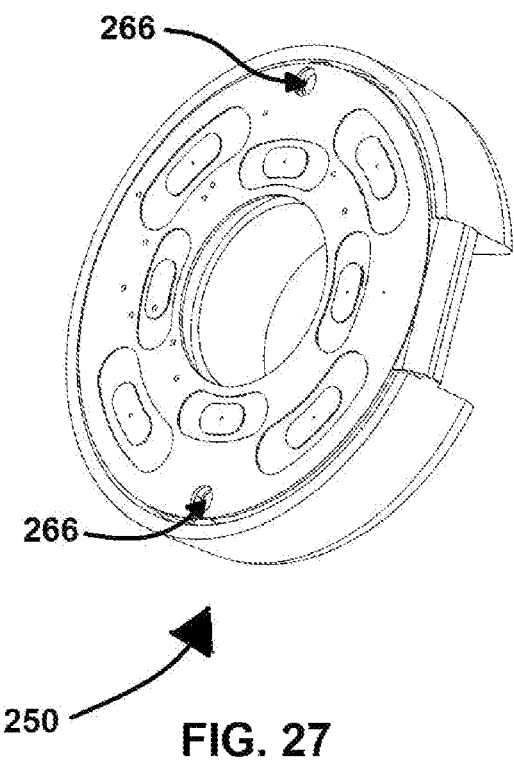
FIG. 27 depicts a perspective view of the distal side of the instrument connector of FIG. 24.
Figure 28:
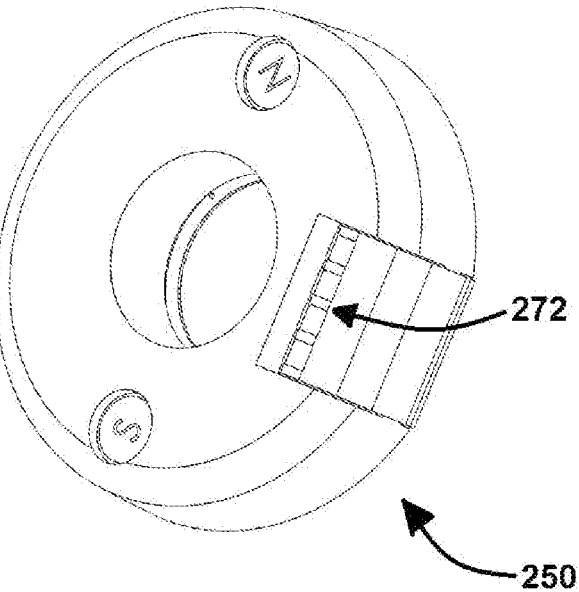
FIG. 28 depicts a perspective view of the proximal side of the instrument connector of FIG. 24.

FPCB cover plate (261) is located atop the elastomeric support member (273) such that the recesses (271) are aligned with the cutouts (275) of the support member and the cavities (269) of the housing (251) (as best seen in FIG. 27), thereby providing the recesses (266) for receiving the bearings (230). In addition, the FPCB cover plate (261) is positioned such that one of the support nubs (278) is located beneath each of the contacts (264A, 264B), and the outer perimeter of the cover plate is positioned atop the rim (276) of the support member (273). The nubs (278) and rim (276) of the support member (273) thus resist inward deflection of the contacts (264A, 264B) as well as inward deflection of the outer portion of the conductive ring (260) of the FPCB cover plate (261) supported by the rim (276). Accordingly, the nubs (278) and rim (276) comprise biasing members that serve to resiliently bias the contacts (264A, 264B) and the outer portion of the conductive ring (260) outwardly (i.e., distally, towards the signal interface adapter (212) during use), thereby facilitating mating, conductive engagement of the contacts on the instrument connector (250) with the contacts on the interface adapter (212). Of course other types of biasing members can be used, such as biasing springs or other resilient features located beneath the contacts and conductive ring.

A ribbon connector (272) extends from the FPCB cover plate (261), and its contacts are in electrical communication with the contacts (260, 264A, 264B), via one or more traces or other conductive pathways provided in one or more of the patterned layers of the FPCB cover plate (261). Ribbon connector (272) is wrapped over the outer edge of the instrument connector (250) and is received within the chamber (280) provided on the housing (251) of the instrument connector. A female connector on a cable similar to cable (52) previously described (not shown) can be operatively attached to the ribbon connector (272), with the other end of the cable operatively connected to the instrument (e.g., to the instrument body) in order to provide electrical communication between the instrument connector (250) and the instrument on which it is mounted.

The modular signal interface system (210) of FIGS. 13-31 is used in a manner similar to that described above for the embodiment of FIGS. 1-8. Once the trocar has been positioned in a patient in the usual manner and the components (212, 250) of the interface system (210) are positioned on the trocar housing and instrument, the instrument shaft is inserted into the cannula through the central aperture (219) of the signal interface adapter (212) (similar to what is depicted in FIG. 1). As the instrument shaft is advanced further into the trocar cannula, the interface adapter (212) and instrument connector (250) will eventually become sufficiently close so that magnetic forces will pull the instrument connector (250) towards the interface adapter (212) along the instrument shaft. The arrangement of the magnetic regions will also induce torque, causing the instrument connector (250) to rotate (as necessary) about the instrument shaft until proper alignment is achieved with respect to the interface adapter (212). As the instrument connector (250) rotates into proper alignment with the interface adapter under the influence of the magnetic regions, the distal face of the instrument connector (250) will ride atop the bearings (230) of the interface adapter until the bearings drop into the recesses (266) (i.e., into apertures (271) and the underlying cavities (269)) of the housing (251)

of the instrument connector. As before, this will also provide an audible click and a tactile indication that mating engagement has been achieved.

Upon such mating engagement, each one of the contacts (264A, 264B) of the instrument connector (250) will be in mating engagement (i.e., contact providing electrical communication) with a corresponding and predetermined one of the contacts (227A, 227B) on the interface adapter. In addition, the conductive ring (260) of the instrument connector will be in mating engagement (i.e., contact providing electrical communication) with the conductive ring (222) on the signal interface adapter.

Figure 32:
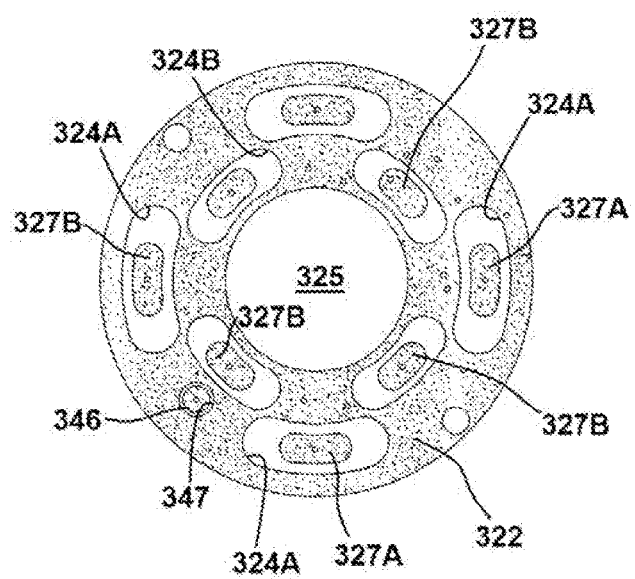
FIGS. 32 and 33 depict alternative embodiments of the conductive ring portions of a signal interface adapter and an instrument connector, respectively.
Figure 33:
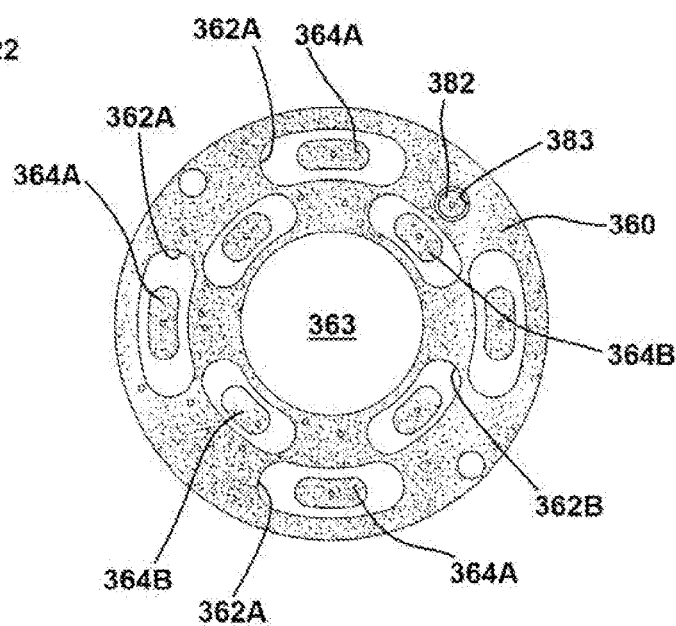

FIGS. 32 and 33 depict alternative embodiments of conductive, mating portions of the PCB or FPCB cover plates of a signal interface adapter and instrument connector, respectively, similar to those provided on components (212, 250) described above. The lined area in FIGS. 32 and 33 simply represent the conductive portions of the PCB/FPCB (e.g., copper) cover plates. Thus, the conductive portions in FIGS. 32 and 33 include conductive rings (322, 360), having central apertures (325, 363), respectively, as well as the additional contacts in the form of conductive oval islands located within apertures provided in the conductive rings (322, 360). Conductive ring (360) of the instrument connector is a mirror image of conductive ring (322) of the signal interface adapter, rotated 180 degrees. Using identical PCB/FPCB cover plates simplifies fabrication, and any differences in electrical connectivity and components of the interface adapter and instrument connector can be provided within their respective housings, beneath the cover plates.

Similar to the previously described embodiments, each conductive ring (322, 360) is annular in shape, and includes a central aperture (325, 363). Each conductive ring (322, 360) also includes a plurality of circumferentially arranged and spaced-apart curved oval apertures (324A, 324B, 362A, 362B), arranged in concentric, spaced-apart bands. Thus, conductive ring (322) of the cover plate for the signal interface adapter has an outer band of spaced-apart curved oval apertures (324A), and an inner band of spaced-apart curved oval apertures (324B), arranged about the a central aperture (325). Similarly, conductive ring (360) of the cover plate for the instrument connector has an outer band of spaced-apart curved oval apertures (362A), and an inner band of spaced-apart curved oval apertures (362B), arranged about the central aperture (363). A plurality of contacts, comprising conductive oval islands (327A, 327B, 364A, 364B) are located within the curved oval apertures (324A, 324B, 362A, 362B), electrically isolated from the rest of the conductive rings (322, 360).

In contrast to the embodiment of FIGS. 13-31, the embodiment of FIGS. 32 and 33 includes one additional communication channel (also known as a communication path or line). In particular, an additional conductive contact (346, 382), also referred to as a guard return contact, is provided on the mating faces of the signal interface adapter and instrument connector, thereby providing a total of ten electrical channels when the components are in mating engagement. Each guard return contact (346, 382) is positioned within an aperture (347, 383) provided in the conductive ring (322, 360), such that the guard return contacts (346, 382) are electrically isolated from the respective conductive rings (322, 360) in which they are located. When the proximal face of the signal interface adapter is in mating engagement with the distal face of the instrument connector, not only will the conductive rings (322, 360) be in conductive contact with each other, each guard return contact (346, 382) will be in conductive contact with a portion of the opposing conductive ring (322, 360) of the other component. Thus, guard returns (346, 382) along with the conductive rings (322, 360) provide a pair of electrical channels that can be used to confirm that the signal interface adapter and instrument connector are properly engaged with one another.

By way of example, the external device (e.g., a generator) or the signal interface adapter itself can apply a small test voltage to guard return contact (346) on the signal interface adapter. If secure, mating engagement has been achieved between the interface adapter and the instrument connector, a corresponding voltage will show up on the line connected to the conductive ring (322) of the signal interface adapter. If no such voltage signal is returned, the external device or the signal interface adapter is configured to assume that there is no secure connection between the interface adapter and instrument connector, and dangerous voltage of current will not be transmitted from the interface adapter. Once a secure connection is detected, the additional communication channel (or line) provided by the guard return contact (382) in mating engagement with the conductive ring (322) provides a second, redundant sense line that is monitored for any stray current or voltage.

Alternatively, instead of (or in addition to) being used to detect proper connection of the two components and stray voltage or current during use, one or both guard returns (346, 382) can be used for identification purposes. For example, guard return (382) on the instrument connector side can be in electrical communication with an integrated circuit chip or similar device located either on the instrument connector or on the surgical instrument that is operatively connected to the instrument connector. The IC chip provides identification information (i.e., a signal) to the external device operatively connected to the signal interface adapter over a dedicated data channel through guard return (383) and guard ring (322). This allows the external device (e.g., a generator) to receive data indicative of, for example, the type of surgical instrument or other pertinent information related to the surgical instrument.

In some embodiments, the signal interface adapter and instrument connector are passive, merely completing a plurality of pathways (i.e., channels) along which signals (power and/or data) are passed between the external electrical device and the surgical instrument. In other embodiments, various electronic circuitry is provided in the signal interface adapter and/or instrument connector such as, for example, an IC chip as described above for identification purposes. Various other circuitry can be included on either of both of the signal interface adapter and instrument connector, such as a 1-wire chip for indicating the presence of the modular signal interface system. Other suitable circuitry can include one or more sensors for detecting various conditions related to the electrical connection of the two components or even for detecting one or more conditions related to the trocar, the surgical instrument or the use of either in a surgical environment.

In still further embodiments, the signal interface adapter (or the trocar housing to which it is attached) can include its own power source (e.g., one or more batteries) for powering the surgical instrument—thus avoiding the need for a connection to an external electrical device via main cable (14). While cordless surgical instruments such as ultrasonic cutting/coagulating devices have been developed, such instruments tend to be heavier and more cumbersome than their corded counterparts due to the added weight of the power supply. This can be avoided by putting the power supply in the signal interface adapter (or the trocar housing to which it is attached). Such an arrangement also allows a single power supply to be used with more than one surgical instrument.

In addition, although embodiments described above use main cable (14) to connect the signal interface adapter to directly to an external electrical device (e.g., a power supply, an RF or ultrasonic generator, etc.), the external electrical device can alternatively comprise a central hub which is operatively connected to one or more additional electrical devices such as generators and the like. The central hub can be used to route signals between the signal interface adapter and one or more of the additional electrical devices. For example, the central hub can be used to translate signals from and to a pre-existing generator (or other electrical device) to suitable signals for the modular signal interface system. In this manner, the modular signal interface system described herein can be used with generators and other electrical devices of multiple types and/or from multiple manufacturers. This is particularly useful when used in conjunction with an arrangement that identifies the type of surgical instrument connected to the modular signal interface system such that the central hub, after identifying the nature of the surgical instrument, routes signals to and from the appropriate generator (or other electrical device).

With respect to the magnetic regions of the two components of the system described herein, any of a variety of materials can be used, particularly neodymium iron boron magnets as well as alnico alloy magnets. In some instances, electromagnets can also be used.

While various embodiments of modular signal interface systems and components thereof have been described in detail above, it will be understood that the components, features and configurations, as well as the methods of manufacturing the devices and methods described herein are not limited to the specific embodiments described herein. For example, in alternative embodiments only the conductive islands, pogo pins or other discrete conductive contacts are used on the mating faces of the two components, without the conductive rings.

What is claimed is:

1. A modular signal interface system for providing electrical communication with a surgical instrument when the surgical instrument is inserted into a cannula of a trocar, the system comprising:
   (a) a signal interface adapter provided on, or adapted to be mounted on the trocar, the signal interface adapter having a central aperture extending therethrough and a proximal face having a plurality of conductive contacts; and
   (b) an instrument connector having a central aperture extending therethrough and a distal face having a plurality of conductive contacts, the instrument connector provided on or adapted to be mounted on a shaft of the surgical instrument such that the shaft is longitudinally and rotatingly movable within the instrument connector, the instrument connector adapted for providing electrical communication between one or more of said contacts of the instrument connector and the surgical instrument on which the instrument connector is provided or mounted;
wherein the signal interface adapter and the instrument connector are adapted for mating engagement such that, when matingly engaged, said central apertures are axially aligned and predetermined ones of the plurality of contacts of the signal interface adapter are in conductive contact with predetermined ones of the plurality of contacts of the instrument connector;
wherein said conductive contacts of each of the signal interface adapter and the instrument connector include a first plurality of spaced-apart contacts arranged about the central apertures thereof; and
wherein the first plurality of conductive contacts of each of the signal interface adapter and instrument connector are circumferentially arranged in a pair of spaced-apart concentric bands.

2. The system of claim 1, further comprising a main cable having one end operatively connected to the signal interface adapter, said main cable having conductors in electrical communication with contacts of the signal interface adapter, said main cable adapted for operative connection to an external electrical device.

3. The system of claim 2, further comprising an instrument cable having conductors in electrical communication with contacts of the instrument connector and operatively connected to or adapted for operative connection to the surgical instrument.

4. The system of claim 1, wherein said signal interface adapter has at least one magnetic region, and said instrument connector has at least one magnetic region, the magnetic regions arranged such that magnetic attraction of said magnetic regions maintains the signal interface adapter and the instrument connector in mating engagement.

5. The system of claim 4 wherein:
   the signal interface adapter includes a pair of magnets disposed on opposite sides of the central aperture thereof and arranged to provide magnetic fields of opposite polarity adjacent the proximal face of the signal interface adapter, and
   the instrument connector includes a pair of magnets disposed on opposite sides of the central aperture thereof and arranged to provide magnetic fields of opposite polarity adjacent the distal face of the instrument connector,
wherein said pairs of magnets are arranged to provide a magnetic force that pulls the signal interface adapter and instrument connector into mating engagement.

6. The system of claim 5, wherein the instrument connector is provided on, or is adapted to be mounted on the shaft of the surgical instrument such that the instrument connector is longitudinally movable along and rotatingly movable about the instrument shaft, and said pairs of magnets are arranged to provide the magnetic force that pulls the instrument connector into mating engagement with the signal interface adapter, with the instrument connector sliding along and rotating about the instrument shaft so as to properly align the contacts of the signal interface adapter and instrument connector.

7. The system of claim 1, wherein at least a portion of the conductive contacts of one or both of the signal interface adapter and the instrument connector are resiliently biased.

8. The system of claim 1, wherein the instrument connector is provided on, or is adapted to be mounted on the shaft of the surgical instrument such that, when the signal interface adapter and the instrument connector are in mating engagement, the shaft is longitudinally and rotatingly movable within the instrument connector while said conductive contact is maintained.

9. The modular signal interface system of claim 1,
   further comprising the trocar, the trocar comprising a trocar cannula housing having a proximal end, with the cannula extending distally from the trocar cannula housing, wherein the signal interface adapter is affixed to the proximal end of the trocar cannula housing.

10. A modular signal interface system for providing electrical communication with a surgical instrument when the surgical instrument is inserted into a cannula of a trocar, the system comprising:
(a) a signal interface adapter provided on, or adapted to be mounted on the trocar, the signal interface adapter having a central aperture extending therethrough and a proximal face having a plurality of conductive contacts; and
(b) an instrument connector having a central aperture extending therethrough and a distal face having a plurality of conductive contacts, the instrument connector provided on or adapted to be mounted on a shaft of the surgical instrument such that the shaft is longitudinally and rotatingly movable within the instrument connector, the instrument connector adapted for providing electrical communication between one or more of said contacts of the instrument connector and the surgical instrument on which the instrument connector is provided or mounted;

wherein the signal interface adapter and the instrument connector are adapted for mating engagement such that, when matingly engaged, said central apertures are axially aligned and predetermined ones of the plurality of contacts of the signal interface adapter are in conductive contact with predetermined ones of the plurality of contacts of the instrument connector;

wherein said conductive contacts of each of the signal interface adapter and the instrument connector include a first plurality of spaced-apart contacts arranged about the central apertures thereof; and wherein said conductive contacts of at least one of said signal interface adapter and instrument connector components further includes at least one apertured planar conductive contact having a plurality of apertures therein, wherein each of the first plurality of contacts of said at least one component are located within the boundary of one of said plurality of apertures such that none of the first plurality of contacts are in conductive contact with said apertured planar conductive contact.

11. The system of claim 10, wherein said conductive contacts of at least one of said components further includes at least one additional conductive contact arranged such that that, when the components are matingly engaged, said at least one additional conductive contact is in conductive contact with the apertured planar conductive contact of the other component.

12. The system of claim 10, wherein one of the signal interface adapter and the instrument connector further includes two or more projections extending away from its distal or proximal face, and the other component includes two or more recesses arranged on its distal or proximal face for receiving said projections when the components are matingly engaged.

13. The system of claim 12 wherein said signal interface adapter has at least one magnetic region, and said instrument connector has at least one magnetic region, the magnetic regions arranged such that mating engagement of the signal interface adapter and the instrument connector results from the magnetic attraction of said magnetic regions.

14. The system of claim 13 wherein:
the signal interface adapter includes a pair of magnets disposed on opposite sides of the central aperture thereof and arranged to provide magnetic fields of opposite polarity adjacent the proximal face of the signal interface adapter, and
the instrument connector includes a pair of magnets disposed on opposite sides of the central aperture thereof and arranged to provide magnetic fields of opposite polarity adjacent the distal face of the instrument connector,
wherein said pairs of magnets are arranged to provide a magnetic force that pulls the signal interface adapter and instrument connector into mating engagement.

15. A signal-associated surgical instrument comprising:
(a) an instrument housing;
(b) an elongate shaft adapted to be received within the interior passageway of a trocar cannula, said shaft extending distally away from said housing; and
(c) an instrument connector having a central aperture extending therethrough and a distal face having a plurality of conductive contacts, said elongate shaft extending through the central aperture of the instrument connector such that the instrument connector is longitudinally and rotatingly movable, with respect to said instrument housing, along and about the shaft;

wherein said conductive contacts of the instrument connector include a first plurality of spaced-apart contacts arranged about the central aperture of the instrument connector;

wherein the first plurality of conductive contacts are circumferentially arranged about the central aperture of the instrument connector in a pair of spaced-apart concentric bands.

16. The signal-associated surgical instrument of claim 15 further comprising a cable having conductors in electrical communication with contacts of the instrument connector, said cable extending between the instrument connector and the instrument housing.

17. The signal-associated surgical instrument of claim 15, wherein said instrument connector further comprises at least one magnetic region.

18. The signal-associated surgical instrument of claim 15, wherein said conductive contacts of said instrument connector further include at least one apertured planar conductive contact having a plurality of apertures therein, wherein each of the first plurality of contacts of said instrument connector are located within the boundary of one of said plurality of apertures such that none of the first plurality of contacts are in conductive contact with said apertured planar conductive contact.

19. The signal-associated surgical instrument of claim 15, wherein said first plurality of contacts of the instrument connector comprise planar contacts.

20. The signal-associated surgical instrument of claim 15 wherein the instrument connector includes a pair of magnets disposed on opposite sides of the central aperture thereof and arranged to provide magnetic fields of opposite polarity adjacent the distal face of the instrument connector.

21. The signal-associated surgical instrument of claim 15, wherein at least a portion of the conductive contacts of the instrument connector are resiliently biased.

* * * * *